United States Patent
Chen et al.

(10) Patent No.: US 10,174,161 B2
(45) Date of Patent: Jan. 8, 2019

(54) TRANSFORMATION OF MESO-LACTIDE

(71) Applicant: Colorado State University Research Foundation, Fort Collins, CO (US)

(72) Inventors: Eugene Y. Chen, Ft. Collins, CO (US); Jian-Bo Zhu, Ft. Collins, CO (US)

(73) Assignee: Colorado State University Research Foundation, Ft. Collins, CO (US)

( * ) Notice: Subject to any disclaimer, the term of this patent is extended or adjusted under 35 U.S.C. 154(b) by 0 days.

(21) Appl. No.: 15/756,670

(22) PCT Filed: Sep. 2, 2016

(86) PCT No.: PCT/US2016/050235
§ 371 (c)(1),
(2) Date: Mar. 1, 2018

(87) PCT Pub. No.: WO2017/041017
PCT Pub. Date: Mar. 9, 2017

(65) Prior Publication Data
US 2018/0244841 A1    Aug. 30, 2018

Related U.S. Application Data

(60) Provisional application No. 62/213,195, filed on Sep. 2, 2015.

(51) Int. Cl.
| | | |
|---|---|---|
| *C08G 63/82* | (2006.01) |
| *C08G 63/08* | (2006.01) |
| *C07D 405/04* | (2006.01) |
| *C07D 515/08* | (2006.01) |
| *C08L 67/04* | (2006.01) |

(52) U.S. Cl.
CPC ......... *C08G 63/823* (2013.01); *C07D 405/04* (2013.01); *C07D 515/08* (2013.01); *C08G 63/08* (2013.01); *C08L 67/04* (2013.01); *C08L 2207/10* (2013.01)

(58) Field of Classification Search
CPC .... C08G 63/823; C08G 63/08; C07D 515/08; C07D 405/04; C08L 67/04; C08L 2207/10
See application file for complete search history.

(56) References Cited

U.S. PATENT DOCUMENTS

| | | |
|---|---|---|
| 6,469,133 B2 | 10/2002 | Baker et al. |
| 8,552,209 B2 | 10/2013 | Benson et al. |
| 9,035,076 B2 | 5/2015 | Benson et al. |
| 2005/0176578 A1 | 8/2005 | Neithamer et al. |
| 2011/0319588 A1 | 12/2011 | Coupin et al. |
| 2012/0095240 A1 | 4/2012 | Benson et al. |
| 2012/0149920 A1 | 6/2012 | Hagen et al. |

OTHER PUBLICATIONS

International Search Report and Written Opinion of the ISA/US dated Dec. 8, 2016 in International Application No. PCT/US2015/050235; 8pgs.
Miyake et al., "Cinchona Alkaloids as Stereoselective Organocatalysts for the Partial Kinetic Resolution Polymerization of rac-Lactide," Macromolecules, 44(11):4116-4124, May 2011.
Zhu et al., "From meso-Lactide to Isotactic Polylactide: Epimerization by B/N Lewis Pairs and Kinetic Resolution by Organic Catalysts," J Am Chem Soc., 137(39):12506-12509, Oct. 2015.

*Primary Examiner* — John M Mauro
(74) *Attorney, Agent, or Firm* — Haukaas Fortius PLLC; Michael H. Haukaas

(57) ABSTRACT

B/N Lewis pairs have been discovered to catalyze rapid epimerization of meso-lactide (LA) or LA diastereomers quantitatively into rac-LA. The obtained rac-LA can be kinetically polymerized into poly(L-lactide) and optically resolved D-LA, with a high stereoselectivity factor $k_L/k_D$ of 53 and an ee value of 91% at 50.6% monomer conversion, by a bifunctional chiral catalyst. The epimerization and enantioselective polymerization can be coupled into a one-pot process for transforming meso-LA directly into poly(L-lactide) and D-LA.

20 Claims, 5 Drawing Sheets

TRANSFORMATION OF MESO-LACTIDE

RELATED APPLICATIONS

This application is a National Stage filing under 35 U.S.C. § 371 of International Application No. PCT/US2016/050235 filed Sep. 2, 2016, which claims priority under 35 U.S.C. § 119(e) to U.S. Provisional Patent Application No. 62/213,195, filed Sep. 2, 2015, which applications are incorporated herein by reference.

GOVERNMENT SUPPORT

This invention was made with government support under grant 1300267 awarded by the National Science Foundation. The government has certain rights in the invention.

BACKGROUND OF THE INVENTION

Poly(lactide) (PLA) is one of the most commercially important biodegradable and biocompatible polymers, with a wide array of applications in packaging, microelectronics, and biomedical fields. Crystalline isotactic PLA (it-PLA) is produced by either ring-opening polymerization (ROP) of S,S-lactide (L-LA) to isotactic poly(L-lactide) (PLLA), or the stereoselective ROP of rac-LA by metal-based catalysts or initiators. The emerging organopolymerization of LA offers a metal-free alternative to the PLA products that are free of residual metal contaminates as desired for biomedical or microelectronic applications. The stereoselective organopolymerization of rac-LA has been achieved by a phosphazene superbase ($^t$Bu-P$_2$) and bulky N-heterocyclic carbenes (NHCs) at low temperatures, and enantioselective or kinetic resolution polymerization of rac-LA by chiral organic catalysts has also been made possible by a cinchona alkaloid and chiral phosphoric acids.

The current industrial PLLA production relies on the large-scale production of L-LA, which is furnished via metal (tin)-catalyzed depolymerization of a low molecular weight (MW) condensation prepolymer of L-lactic acid. However, this process affords a mixture of LA stereoisomers containing that are predominately L-LA but also a considerable amount of meso-LA as a by-product or waste that needs to be removed from the rest of the LA stream, seriously affecting the economy of the manufacturing of PLLA. In addition, as a possible feedstock-recycling pathway, thermal degradation of PLLA produced many kinds of degradation products including LA diastereomers (rac-LA/meso-LA=2/1), cyclic oligomers and their diastereomers, as well as $CO_2$, CO, $CH_3CHO$, and $CH_2$=CHCOOH. Hence, racemization causes a serious problem with the feedstock recycling and the reproduction of PLLA. The optical purity of LA significantly affects the materials properties of the PLLA produced by ROP, and any incorporation of meso-LA into the PLLA product will significantly alter or deteriorate the properties of the PLLA materials such as crystallinity and biodegradation rate.

The ROP of meso-LA typically forms predominantly atactic, amorphous PLA, but the stereoselective ROP of meso-LA has led to syndiotactic PLA (st-PLA) or amorphous heterotactic PLA. The crystalline st-PLA has a melting-transition temperature ($T_m$) of ~150° C., which is about 20-30° C. lower than that of it-PLA produced by either ROP of L-LA or stereoselective ROP of rac-LA, thus an inferior material. Hence, it is of great interest to be able to catalytically isomerize meso-LA to rac-LA. However, the epimerization under base-catalyzed homogeneous conditions is controlled by the equilibrium between meso-LA and rac-LA, achieving only an equilibrium mixture; citing the state-of-the-art example here, epimerization of meso-LA by sodium ethylhexanoate (0.05%) in bulk at 160° C. for 15 h afforded a mixture containing 36% L-LA+36% D-LA+28% meso-LA, plus 0.5 wt % linear oligomers (see U.S. Pat. No. 9,035,076 (Benson et al.)). Accordingly, there is a need for a solution to the challenges facing the effective utilization of meso-LA.

SUMMARY

The invention provides a new method to utilize the "waste" side-product of the industrial L-lactide (L-LA) production process, meso-lactide (meso-LA), by transforming it into the valuable monomer racemic lactide (rac-LA), or directly into crystalline isotactic polylactide (it-PLA). The epimerization of meso-LA to rac-LA can be achieved by use of a variety of Lewis Pairs, typically in a catalytic amount, either in solution or in a bulk melt. Isotactic polylactide can then be readily prepared using kinetic resolution by the organic catalysts described herein.

The invention therefore provides a method to epimerize meso-lactide into racemic lactide comprising contacting meso-lactide and a Lewis acid/base pair for a period of time sufficient to epimerize meso-lactide to racemic lactide. The Lewis acid/base pair can present in at least about 0.001 mol % of the with respect to the initial molar amount of meso-lactide.

In one embodiment, the Lewis acid/base pair is a boron/nitrogen Lewis acid/base pair. For example, the Lewis acid of the Lewis acid/base pair can be $B(C_6F_5)_3$, and the Lewis base of the Lewis acid/base pair can be 1,4-diazabicyclo[2.2.2]octane (DABCO) or triethylamine. Even under crude reaction conditions, at least about 50%, or at least about 80%, of the meso-lactide is epimerized into racemic lactide. Starting from pure meso-lactide, typically at least about 80%, or at least about 90%, of the meso-lactide is epimerized into racemic lactide.

The contacting of the meso-lactide and the Lewis acid/base pair can be carried out in solution or in bulk phase. When the contacting is carried out in the presence of solvent, such as toluene, the solvent can be selected such that meso-lactide is soluble in the solvent at 25° C. and racemic lactide is not soluble in the solvent at 25° C. In one embodiment, the initial concentration of the meso-lactide in the solvent is at least about 0.2 M. In another embodiment, the meso-lactide in the solvent is about 1 M to about 3 M.

When the contacting of the meso-lactide and the Lewis acid/base pair is in solution, the method can be carried out at about 0° C. to about 100° C. The contacting of the meso-lactide and the Lewis acid/base pair can also be carried out in bulk phase (i.e., in the absence of solvent, or when the amount of solvent is insufficient to solubilize the meso-lactide). When the contacting of the meso-lactide and the Lewis acid/base pair is carried out in bulk phase, the meso-lactide can be heated to a temperature of at least about 54° C. but not more than about 116° C.

In a typical epimerization reaction, the concentration of the Lewis acid/base pair is about 10 ppm (based on moles of meso-lactide and moles of the Lewis acid/base pair) to about 5 mol % with respect to the meso-lactide.

The methods can further comprise isolating substantially pure racemic lactide after meso-lactide has been epimerized into racemic lactide, wherein the isolating comprises one or more of filtering, washing, and chromatographing the racemic lactide.

The methods can also further comprise kinetic resolution of the racemic lactide by contacting the racemic lactide with a compound of Formula I:

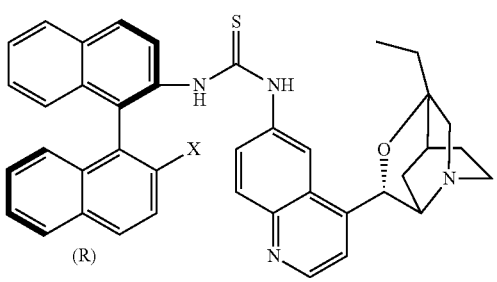

(I)

wherein X is —NH—C(=O)—R, wherein R is —CH$_3$, —CF$_3$, 2-propenyl, or optionally substituted aryl; under suitable conditions to initiate ring-opening polymerization of L-lactide to provide a mixture of isotactic poly(L-lactide) and D-lactide. In one embodiment, the compound of Formula I is compound 4:

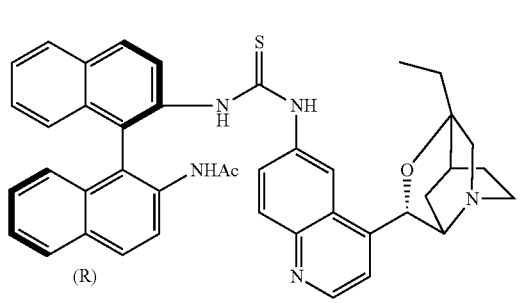

(4)

The methods can further comprise separating the isotactic poly(L-lactide) and D-lactide, and optionally purifying the isotactic poly(L-lactide) and D-lactide.

In some embodiments, the meso-lactide, prior to epimerization, is in a composition that comprises one or more impurities selected from racemic lactide, lactic acid, lactic acid salts, and oligomers of lactide (e.g., plant grade meso-lactide, and/or the (optionally crude) product of preparing lactide from lactic acid). The composition that comprises one or more impurities can be treated, prior to epimerization, by a method comprising contacting the composition with about 1 mol % to about 10 mol % of AlCl$_3$ prior to contacting the meso-lactide with the Lewis acid/base pair. The composition, after having been contacted with the AlCl$_3$, can be purified prior to carrying out the epimerization reaction.

In a further embodiment, the invention provides a compound of Formula I:

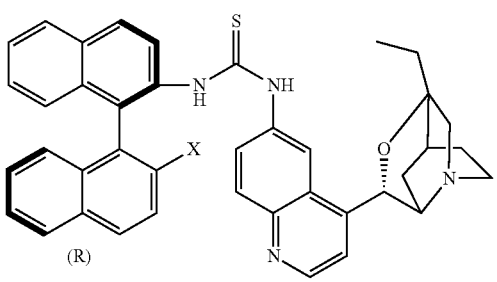

(I)

wherein X is —NH—C(=O)—R, wherein R is —CH$_3$, —CF$_3$, 2-propenyl, or optionally substituted aryl. The invention further provides novel compounds of Formula I, intermediates for the synthesis of compounds of Formula I, as well as methods of preparing compounds of Formula I.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
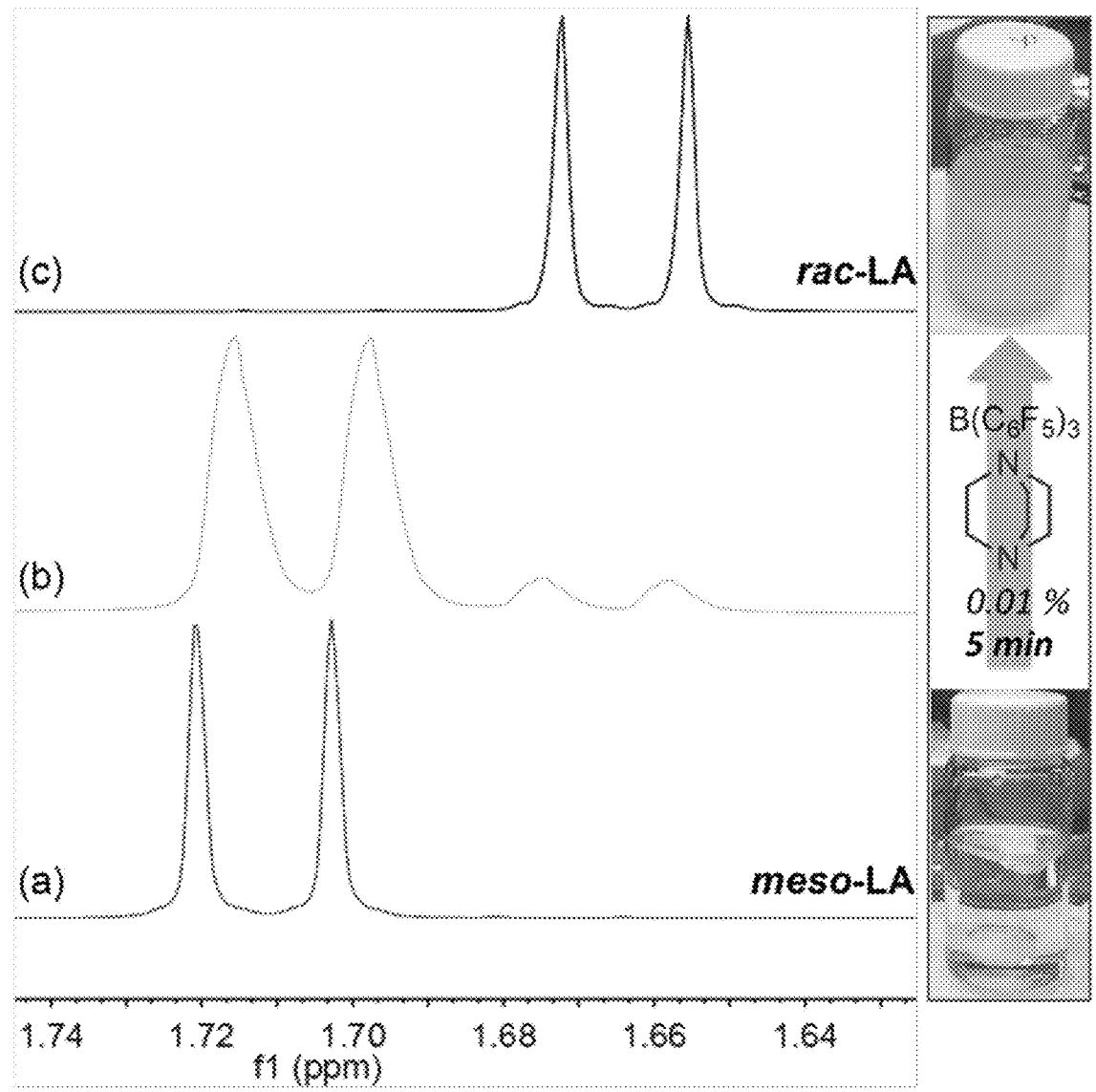
FIG. 1. Left: NMR spectra (CDCl$_3$) of the methyl region of: (a) pure meso-LA; (b) meso-LA/rac-LA (90/10) from Nature Works; and (c) isolated pure rac-LA from epimerization of meso-LA. Right: pictorial representation of fast epimerization of meso-LA to rac-LA (which precipitates out of solution) by DABCO/B(C$_6$F$_5$)$_3$ (2.88 g scale, 2.0 M in toluene, 5 min, 95.4% conversion).

B/N Lewis pairs have been discovered to catalyze rapid epimerization of meso-lactide (LA) or LA diastereomers quantitatively into rac-LA. The rac-LA can be prepared in solution or in bulk (solvent free conditions). The obtained rac-LA can be kinetically polymerized into poly(L-lactide) and optically resolved D-LA, with a high stereoselectivity factor $k_L/k_D$ of 53 and an ee value of 91% at 50.6% monomer conversion, by newly designed bifunctional chiral catalyst 4 that incorporates three key elements (β-isocupreidine core, thiourea functionality, and chiral BINAM) into a single organic molecule. The epimerization and enantioselective polymerization can be coupled into a one-pot process for transforming meso-LA directly into poly(L-lactide) and D-LA.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation oft 5%, ±10%, ±20%, ort 25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture, such as rac-LA or it-PLA. Thus, an "effective amount" generally means an amount that provides the desired effect.

Embodiments of the Invention

The invention provides methods to epimerize meso-lactide into racemic lactide. The methods include contacting meso-lactide and a Lewis acid/base pair for a period of time sufficient to epimerize meso-lactide to racemic lactide. The meso-lactide can be a composition of pure meso-lactide, or the meso-lactide can be in a composition that includes any amount of racemic lactide. Such mixtures of meso-lactide and racemic lactide are often obtained from industrial processes at ratios of meso-lactide to racemic lactide of about 1/9. However, the epimerization reaction can be carried out on a composition that has any ratio of meso-lactide to racemic lactide. A significant advantage of epimerization by the methods described herein is that the epimerization occurs without the formation of any detectable oligomeric lactide, which greatly increases the value of the resulting meso-lactide and simplifies purification of the meso-lactide product.

In a typical epimerization of meso-lactide, at least about 0.001 mol % of the Lewis acid/base pair is present with respect to the initial molar amount of meso-lactide. The reaction can be carried out for one to a few minutes, up to several days. However, the reaction in solution is typically complete in several (5-10) minutes, or within several (1-10) hours. As described herein, various Lewis acid/base pairs can be used for the epimerization, as well as a variety of different solvent and reaction conditions. In a typical reaction, at least about 50%, at least about 80%, at least about 90%, of the meso-lactide is epimerized into racemic lactide. Under suitable conditions, the conversion of meso-lactide to racemic lactide (epimerization) is near quantitative, which can be defined as greater than or equal to 98%.

The methods can also include isolating substantially pure racemic lactide after meso-lactide has been epimerized into racemic lactide. The isolating can include one or more of filtering, washing, and chromatographing the racemic lactide, or another suitable technique for isolating and/or purifying the meso-lactide such as distillation or sublimation. Useful techniques for isolation of meso-lactide are described in U.S. Pat. No. 9,035,076 (Benson et al.), which is incorporated herein by reference to the extent not inconsistent with this disclosure.

A generic racemization and polymerization scheme starting from meso-LA is shown below in Scheme 1. The products can be rac-LA (i.e., a combination of L-LA and D-LA) or the final polymer materials and an optically resolved monomer (e.g., a mixture of isotactic poly(L-lactide) and D-lactide, or a mixture of isotactic poly(D-lactide) and L-lactide). Additional embodiments include variations in the structures of the racemization catalyst and the stereoselective polymerization catalyst, as well as in the epimerization and polymerization processes.

Lewis Pair Catalysts for Racemization of meso-LA to rac-LA.

Effective catalysts are those Lewis acid/base pairs, a Lewis acid and base employed together to promote the transformation of meso-LA to rac-LA (added to a reaction mixture separately or together), while the acid without the base, or vice versa, is ineffective or far less effective for the racemization under the conditions described herein. Lewis acids include, but are not limited to, $B(C_6F_5)_3$ and its derivatives (e.g., $B(C_6H_5)_3$, $ClB(C_6F_5)_2$, and the like), $Al(C_6F_5)_3$ and its derivatives (e.g., $Al(C_6H_5)_3$, $ClAl(C_6F_5)_2$, and the like), $AlCl_3$, and the like. Lewis bases include, but are not limited to, DABCO, $Et_3N$ (or other trialkyl amines), 1-azabicyclo[2.2.2]octane (ABCO), PMP, heterocyclic or heteroaryl amines, etc. The catalyst can be immobilized on a solid support such as silica, alumina, a polymer, or clay.

In one embodiment, the Lewis acid/base pair is a boron/nitrogen Lewis acid/base pair. In some embodiments, the Lewis acid of the Lewis acid/base pair is $B(C_6F_5)_3$. In various embodiments, the Lewis base of the Lewis acid/base pair is 1,4-diazabicyclo [2.2.2]octane (DABCO) or triethylamine.

Process.

For epimerization in solution, the epimerization is typically carried out at ambient temperature with a suitable solvent (relatively non-polar solvents such as toluene, xylenes, or benzene) and sufficiently high initial meso-LA concentration (such as 2.0 M) so that the resulting rac-LA product can precipitate from solution, which is a key to driving the epimerization reaction to completion. This reaction typically starts from a clear solution and then gradually becomes heterogeneous as the rac-LA product builds up and crashes out of solution. In certain embodiments, the epimerization can be run at about 0° C. to about 100° C., about 10° C. to about 60° C., about 15° C. to about 40° C., about 20° C. to about 30° C., or at about 25° C. At the end of reaction, from minutes to hours, a simple filtration can separate the desired product rac-LA in its pure state, and the resulting filtrate, which contains predominantly rac-LA, can be reused for the subsequent racemization reaction.

The epimerization reaction can also be carried out in bulk (no solvent) at higher temperatures such as at about 53° C. to about 117° C., 54° C. to about 116° C., 60° C. to about 100° C., or preferably about 70° C. to about 85° C. In various embodiments, the epimerization can be run at about 65° C. to about 90° C., about 67° C. to about 88° C., about 68° C. to about 85° C., about 68° C. to about 80° C., about 68° C. to about 75° C., or at about 70° C.

In one embodiment, the contacting is carried out in the presence of solvent, such as toluene, wherein meso-lactide is soluble in the solvent at 25° C. and racemic lactide is not soluble in the solvent at 25° C. The initial concentration of the meso-lactide in the solvent can be at least about 0.2 M. In various embodiments, the initial concentration of the meso-lactide in the solvent is at least 1 M, for example, about 1 M to about 3 M, or about 2M.

In various embodiments, the concentration of the Lewis acid/base pair is about 10 ppm to about 10 mol % with respect to the meso-lactide. Typically, the concentration of the Lewis pair is about 5 mol %, about 2.5 mol %, about 1 mol %, about 0.1 mol %, about 0.01 mol %, or about 0.001 mol %, based on the molar amount of initial meso-lactide (individually and independently of each component of the Lewis pair, although typically about 1:1, and therefore one of the pair may actually be in excess wherein only a portion of that Lewis acid or base is thus paired).

Chiral Organic Catalysts for Stereoselective Polymerization of rac-LA.

The chiral organic catalysts that can perform effective kinetic resolution polymerization of rac-LA into isotactic poly(L-lactide) and optically resolved D-LA, or vice versa, are those catalysts incorporating three essential elements into a single organic catalyst molecule (e.g., catalyst 4 described above): β-isocupreidine (β-ICD) core, thiourea functionality, and binaphthyl-amine (BINAM). These are bifunctional chiral catalysts, carrying a chiral double H-bonding donor based on the BINAM framework for asymmetric activation of the monomer (by the chiral acid) and the propagating P—OH specie (by the chiral amine β-ICD). Natural extension of such catalysts includes structural modifications of the catalyst by derivating the β-ICD core, the thiourea functionality, and/or the BINAM framework.

Accordingly, the methods of the invention include contacting racemic-lactide with a catalyst as described herein to provide a mixture of isotactic poly(L-lactide) and D-lactide. In another embodiment, the method provides a mixture of isotactic poly(D-lactide) and L-lactide. The methods thus include kinetic resolution of racemic lactide by contacting the racemic lactide with a chiral organic catalyst, such as a compound of Formula I:

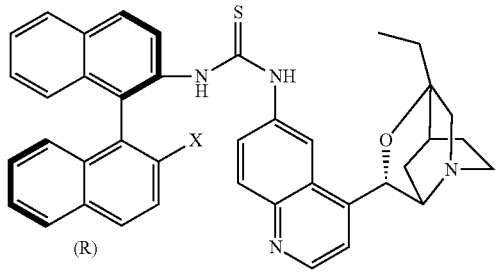

(I)

wherein X is —NH—C(=O)—R, wherein R is —CH₃, —CF₃, 2-propenyl, or optionally substituted aryl (e.g., phenyl substituted with one or more trifluoromethyl or trifluoromethoxy groups, in one or more of the ortho, meta, or para positions of the phenyl); under suitable conditions to initiate ring-opening polymerization of L-lactide to provide a mixture of isotactic poly(L-lactide) and D-lactide. In one specific embodiment, the catalyst of Formula I is compound 4:

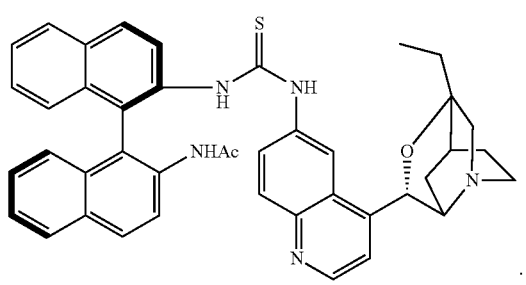

(4)

The methods can further include separating the isotactic polylactide and D-lactide (or L-lactide). The meso-lactide, prior to epimerization, can be in a composition that comprises one or more impurities selected from racemic lactide, lactic acid, lactic acid salts, and oligomers of lactide. That composition can be treated, prior to epimerization, by a method comprising contacting the composition with about 1 mol % to about 10 mol %, typically about 5 mol %, of a Lewis acid such as AlCl₃ prior to contacting the meso-lactide with the Lewis acid/base pair for epimerization. This pretreatment can aid the removal of lactic acid, lactic acid salts, and oligomers of lactide to increase the conversion in the epimerization reaction. After pretreatment of crude or plant grade lactide, the pretreated lactide can then optionally be purified by filtration, distillation, or sublimation, prior to carrying out the epimerization reaction. The two processes, epimerization and stereoselective polymerization (kinetic resolution), can be coupled together and carried out in a one-pot fashion, thus effectively converting meso-LA directly into either isotactic crystalline polylactide or isotactic crystalline poly(L-lactide) and D-LA.

From meso-Lactide to Isotactic Polylactide: Epimerization by B/N Lewis Pairs and Kinetic Resolution by Organic Catalysts In view of the challenges facing effective utilization of meso-LA, we devised a strategy for conversion of meso-LA directly into the desired product it-PLA by organic catalysts, through a two-step process that can be carried out in a one-pot fashion: epimerization of meso-LA to rac-LA, followed by stereoselective or enantioselective polymerization (Scheme 1). To realize this strategy, one must first develop an epimerization reaction that can achieve quantitative conversion of meso-LA to rac-LA and then discover an enantioselective catalyst that can perform the effective kinetic resolution polymerization of rac-LA.

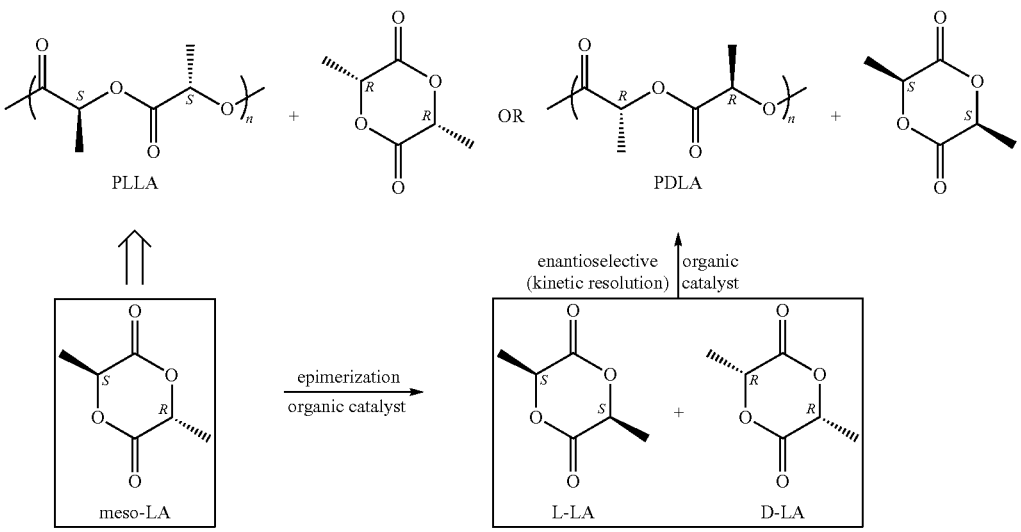

Scheme 1. New strategy for utilization of meso-LA.

To the first task, we reasoned that the dynamic meso-LA⇔rac-LA equilibrium should be controlled by temperature, base, solvent, and solubility difference. For instance, carrying out the epimerization at lower temperatures (e.g., 25° C. or room temperature, RT) should shift the equilibrium further towards rac-LA and also avoid any LA oligomerization, and finding conditions that can continuously remove the formed rac-LA from the reaction mixture should drive the epimerization to completion. However, an immediate challenge was the epimerization rate at RT is too low to be practical. Indeed, our initial screening of some potent base catalysts such as quinidine (QD), β-isoquinidine (β-IQD), 1,4-diazabicyclo [2.2.2]octane (DABCO), and 1,8-diazabicyclo[5.4.0]undec-7-ene (DBU) for the meso-LA epimerization reaction with 2 mol % base at RT rendered no or negligible epimerization after up to 2 days of reaction, or just resulted in polymerization (by DBU).

Inspired by the "frustrated Lewis pair" (FLP) chemistry (Stephan et al., Angew. Chem. Int. Ed. 2015, 54, 6400-6441; Stephan et al., Angew. Chem. Int. Ed. 2010, 49, 46-76) that takes advantage of the unquenched, orthogonal Lewis acid and Lewis base reactivity for FLP-type activation of small molecules or tandem catalysis (FLP- and classical LP working in concert) in polymerization of polar monomers (Chen et al., Angew. Chem. Int. Ed. 2015, 54, 6842-6846; Xu and Chen, J. Polym. Sci. Part A: Polym. Chem. 2015, 53, 1895-1903), we turned our attention to investigations into LPs for meso-LA epimerization. Like the above Lewis bases, Lewis acids such as $B(C_6F_5)_3$, when used alone, exhibited no activity. Excitingly, when combined together, the LP DABCO/$B(C_6F_5)_3$ catalyzes rapid, essentially quantitative epimerization of meso-LA to rac-LA (FIG. 1).

When carried out in $CH_2Cl_2$ (1.0 M) by DABCO/B$(C_6F_5)_3$ (2.0 mol %), the meso-LA epimerization reaction achieved a maximum meso-to-rac-LA conversion of 82%. Starting with rac-LA under the same conditions formed the same mixture of rac/meso lactides in a ratio of ca. 82:18. Variations of acids and bases showed that DABCO/B$(C_6F_5)_3$ and $Et_3N$/B$(C_6F_5)_3$ performed similarly and appeared to give the best conversion (Table A). Thus, one of these LPs, DABCO/B$(C_6F_5)_3$, was used for further optimization. Changing the solvent to more polar, donor solvents such as DMF and DMSO drastically lowered the conversion to ~20% or below. On the other hand, use of the relatively non-polar toluene, which enabled precipitation of rac-LA from solution once formed markedly enhanced the meso-to-rac-LA conversion to 95%. Increasing the initial [meso-LA]$_0$ concentration from 0.2 M to 0.5, 1.0, 1.5 and 2.0 M resulted in a steady increase in the conversion from 86% to 93, 95, 97, and 98%, respectively (Table A). While keeping the concentration at 2.0 M, we gradually lowered the LP loading from 2.0 mol % to 1.0, 0.5, 0.2, 0.1, 0.05, 0.01, 0.005, and 0.002 mol % (i.e., 20 ppm), and found the meso-to-rac-LA conversion still remained at an essentially quantitative level of 97-99%.

TABLE A

Results of Epimerization of Meso-LA with Lewis Pairs

| Run | Acid | Base | Solvent [a] | meso-LA/LA/LB | Time (h) | Conv. (%) [b] |
|---|---|---|---|---|---|---|
| 1 | $AlCl_3$ | DABCO | DCM (1M) | 50/1/1 | 11 | 7.6 |
| 2 | $ZnCl_2$ | DABCO | DCM (1M) | 50/1/1 | 11 | 0 |
| 3 | $BCl_3$ | DABCO | DCM (1M) | 50/1/1 | 12 | 0 |
| 4 | $TiCl_4$ | DABCO | DCM (1M) | 50/1/1 | 12 | 0 |
| 5 | $CuCl_2$ | DABCO | DCM (1M) | 50/1/1 | 12 | 0 |
| 6 | $FeCl_3$ | DABCO | DCM (1M) | 50/1/1 | 12 | 0 |
| 7 | $LaCl_3$ | DABCO | DCM (1M) | 50/1/1 | 12 | 0 |
| 8 | La(OTf)$_3$ | DABCO | DCM (1M) | 50/1/1 | 12 | 0 |
| 9 | Sc(OTf)$_3$ | DABCO | DCM (1M) | 50/1/1 | 12 | 0 |
| 10 | TMP-ITC | ABCO | DCM (1M) | 50/1/1 | 32 | 20.3 |
| 11 | HB$(C_6F_5)_2$ | DABCO | DCM (1M) | 50/1/1 | 12 | 0 |
| 12 | ClB$(C_6F_5)_2$ | DABCO | DCM (1M) | 50/1/1 | 12 | 14.8 |
| 13 | B$(C_6F_5)_3$ | DABCO | DCM (1M) | 50/1/1 | 11 | 82 |
| 14 | B$(C_6F_5)_3$ | DABCO | DCM (1M) | 50/1/1 | 33 | 82 |
| 15 | B$(C_6F_5)_3$ | — | DCM (1M) | 50/1/1 | 11 | 0 |
| 16 | — | DABCO | DCM (1M) | 50/1/1 | 11 | 0 |
| 17 | B$(C_6F_5)_3$ | PMP | DCM (1M) | 50/1/1 | 11 | 37.7 |
| 18 | B$(C_6F_5)_3$ | $Et_3N$ | DCM (1M) | 50/1/1 | 11 | 81.9 |
| 19 | B$(C_6F_5)_3$ | DMAP | DCM (1M) | 50/1/1 | 11 | 0 |
| 20 | B$(C_6F_5)_3$ | DTBP | DCM (1M) | 50/1/1 | 11 | 0 |
| 21 | B$(C_6F_5)_3$ | I$^t$Bu | TOL (2M) | 10000/1 | 11 | 0 |
| 22 | B$(C_6F_5)_3$ | DABCO | DMSO (1M) | 50/1/1 | 11 | 20.4 |
| 23 | B$(C_6F_5)_3$ | DABCO | DMF (1M) | 50/1/1 | 11 | 17.1 |
| 24 | B$(C_6F_5)_3$ | DABCO | TOL (0.2M) | 50/1/1 | 11 | 86.4 |
| 25 | B$(C_6F_5)_3$ | DABCO | TOL (0.5M) [c] | 50/1/1 | 22 | 93.0 |
| 26 | B$(C_6F_5)_3$ | DABCO | TOL (1M) [c] | 50/1/1 | 22 | 94.5 |
| 27 | B$(C_6F_5)_3$ | DABCO | TOL (1.5M) [c] | 50/1/1 | 22 | 97.1 |
| 28 | B$(C_6F_5)_3$ | DABCO | TOL (2M) [c] | 50/1/1 | 22 | 97.6 |
| 29 | B$(C_6F_5)_3$ | DABCO | TOL (2M) [c] | 100/1/1 | 22 | 97.7 |
| 30 | B$(C_6F_5)_3$ | DABCO | TOL (2M) [c] | 200/1/1 | 22 | 97.8 |
| 31 | B$(C_6F_5)_3$ | DABCO | TOL (2M) [c] | 500/1/1 | 22 | 98.1 |
| 32[d] | B$(C_6F_5)_3$ | DABCO | TOL (2M) [c] | 500/1/1 | 22 | 98.0 |
| 33[e] | B$(C_6F_5)_3$ | DABCO | TOL (2M) [c] | 500/1/1 | 22 | 98.3 |
| 34[f] | B$(C_6F_5)_3$ | DABCO | TOL (2M) [c] | 500/1/1 | 22 | 98.4 |
| 35 | B$(C_6F_5)_3$ | DABCO | TOL (2M) [c] | 1000/1/1 | 22 | 97.8 |
| 36 | B$(C_6F_5)_3$ | DABCO | TOL (2M) [c] | 2000/1/1 | 22 | 98.0 |
| 37 | B$(C_6F_5)_3$ | DABCO | TOL (2M) [c] | 10000/1/1 | 22 | 99.1 |
| 38 | B$(C_6F_5)_3$ | DABCO | TOL (2M) [c] | 10000/1/1 | 0.083 | 95.4 [g] |
| 39 | B$(C_6F_5)_3$ | DABCO | TOL (2M) [c] | 20000/1/1 | 22 | 97.9 |

TABLE A-continued

Results of Epimerization of Meso-LA with Lewis Pairs

| Run | Acid | Base | Solvent [a] | meso-LA/LA/LB | Time (h) | Conv. (%) [b] |
|---|---|---|---|---|---|---|
| 40 | B(C$_6$F$_5$)$_3$ | DABCO | TOL (2M) [c] | 50000/1/1 | 22 | 98.6 [h] |
| 41 | B(C$_6$F$_5$)$_3$ | DABCO | TOL (2M) [c] | 50000/1/1 | 10 | 88.2 [i] |
| 42[j] | B(C$_6$F$_5$)$_3$ | DABCO | Bulk | 1000/1/1 | 2 | 96.5 |
| 43[j] | B(C$_6$F$_5$)$_3$ | DABCO | Bulk | 10000/1/1 | 10 | 93.7 |

[a] Concentration of meso-LA is given in parentheses.
[b] Determined by $^1$H NMR in CDCl$_3$.
c Heterogeneous reaction.
[d] Rac-LA/meso-LA = 1/9 as starting material.
[e] Rac-LA/meso-LA = 1/1 as starting material.
[f] Rac-LA/meso-LA = 9/1 as starting material.
[g] TOF = 114480 h$^{-1}$.
[h] Isolated yield by column chromatography, rac-LA/meso-LA = 55.4/1.
[i] Isolated yield as pure rac-LA by simple filtration.
[j] At 70° C.

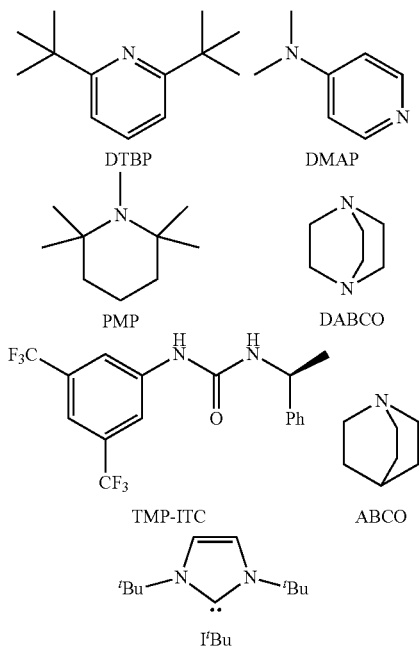

Figure 3:
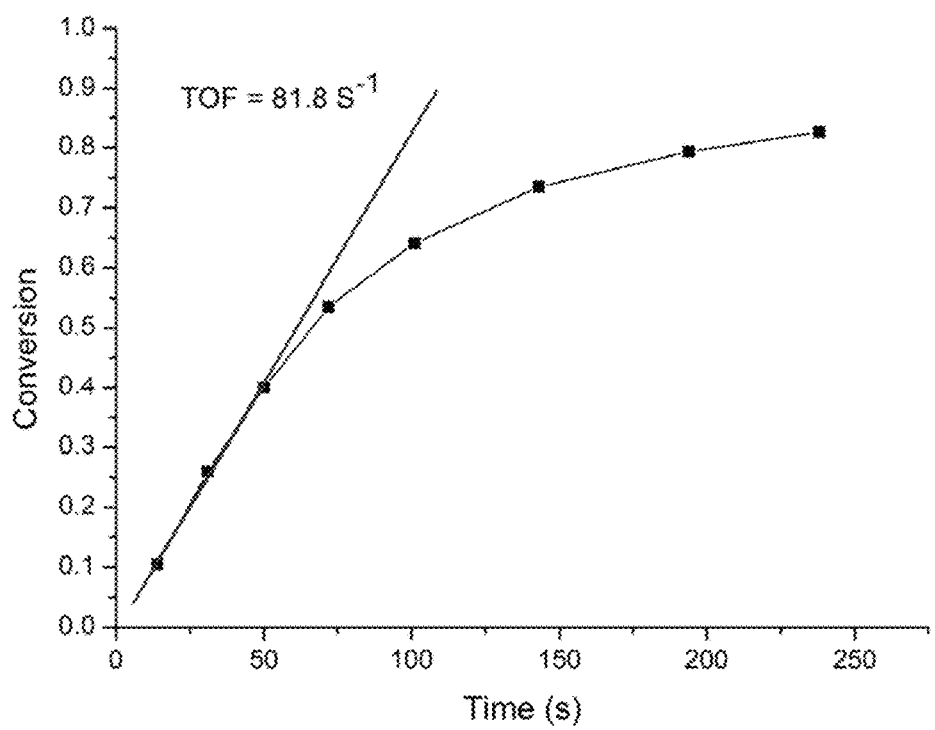
FIG. 3. Conversion-time plot of the epimerization of meso-LA to rac-LA by Lewis pair DABCO/B(C$_6$F$_5$)$_3$ (2.0 M in toluene, 0.01 mol % LP catalyst, RT).

The epimerization is rapid, as shown by the reaction with 0.01 mol % of the LP, which achieved 95.4% meso-to-rac-LA conversion in just 5 min (FIG. 1). To more accurately assess the rate of the epimerization, the reaction was stopped at different times and the conversion-time plot gave a very high turnover-frequency of 81.8 s$^{-1}$ or 2.95×10$^{-1}$ (FIG. 3). The epimerization can also be carried out in bulk at 70° C., still achieving a high meso-to-rac-LA conversion of 94-97%, depending on catalyst loading and reaction time (Table A). At this temperature, precipitation of rac-LA from meso-LA shifts the equilibrium further towards rac-LA. This LP-catalyzed epimerization worked similarly, irrespective of the initial meso-LA/rac-LA ratio in the feed (Table A).

Isolation of the epimerization product was performed on a 5.76 g scale of the reaction with 20 ppm catalyst loading in toluene at RT; upon completion of the reaction, simple filtration, followed by washing with cold toluene and drying under vacuum, afforded the pure rac-LA in 88.2% isolated yield. The filtrate was a mixture of rac-LA (95%) and meso-LA (5%), which can be reused for the epimerization.

Alternatively, the crude epimerization product was purified by flash chromatography on silica gel to give rac-LA (>98% purity) in 98.6% yield.

This observed remarkable performance of the LP is presumably due to the cooperativity of the LP in that the [B] Lewis acid activates the substrate meso-LA via carbonyl coordination, which accelerates the deprotonation at the tertiary carbon of the activated substrate by the [N] base (I), leading the planar enolate intermediate (II) that can be reprotonated causing epimerization.

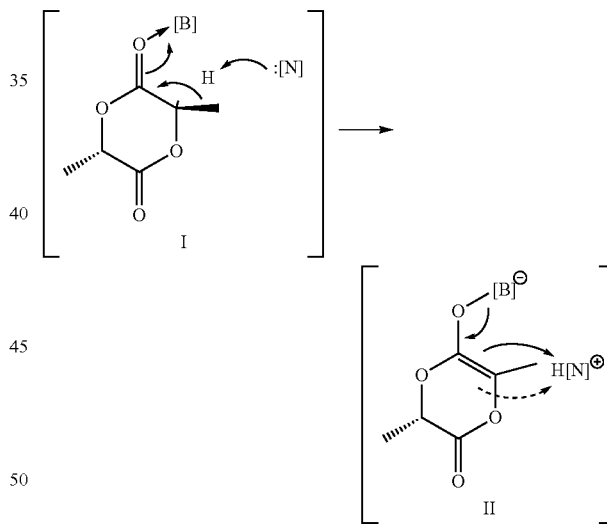

An alternative mechanism that possibly involves reshuffling of the two halves of the lactide by transesterification was excluded as the same mixture of rac/meso lactides in a ratio of ca. 82:18 was formed when homochiral L-LA was treated under the same epimerization conditions as described above for the meso-LA. Noteworthy is that use of the preformed classical Lewis adduct (insoluble) DABCO.B(C$_6$F$_5$)$_3$ (Eisenberger et al., *J. Am. Chem. Soc.* 2012, 134, 17384-17387) performed identically to the current standard procedure that premixes the borane with meso-LA, followed by addition of DABCO to start the reaction. This result indicates that, under the current catalytic conditions, this adduct can reversibly and rapidly dissociate into the respective base and acid to catalyze the epimerization.

Having achieved the first task of quantitative epimerization of meso-LA to rac-LA, we tackled the second task of developing an enantioselective catalyst that can perform the effective kinetic resolution polymerization of rac-LA. We reasoned that the bifunctional β-isocupreidine (β-ICD), which represents the first example of organocatalytic enantioselective polymerization of rac-LA but with a low stereoselectivity factor ($s=k_S/k_R$ or $k_L/k_D$) of 4.4 and a low ee value of 45.1% (kinetically resolved D-LA) at 48.4% monomer conversion (Miyake and Chen, *Macromolecules* 2011, 44, 4116-4124), could be modified or redesigned into advanced chiral organic catalysts with potentially much higher stereoselectivity.

Figure 6:
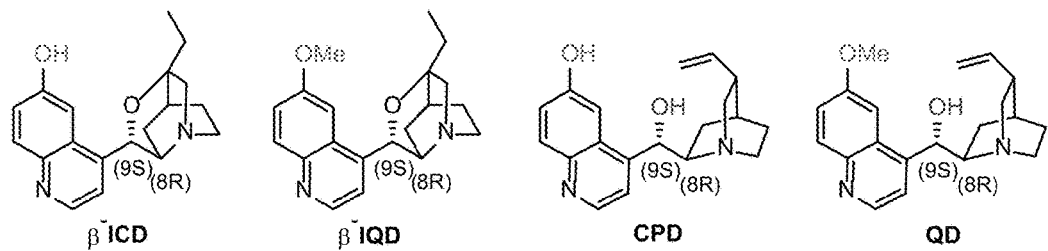
FIG. 6. Structures of chiral organic catalysts used for kinetic resolution polymerization of rac-LA in this study.
Figure 6:
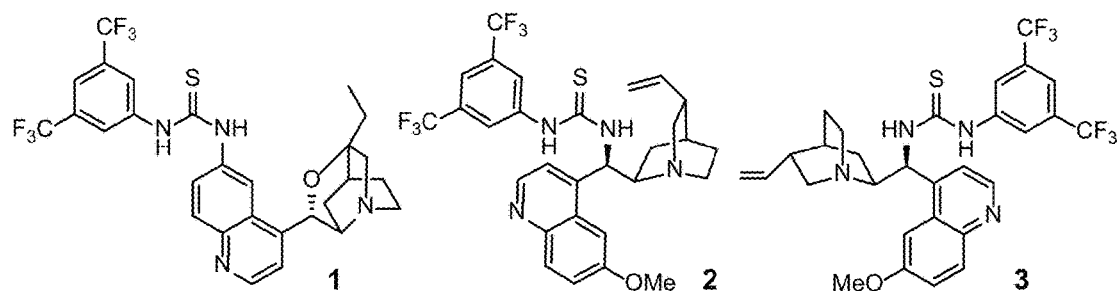
Figure 6:
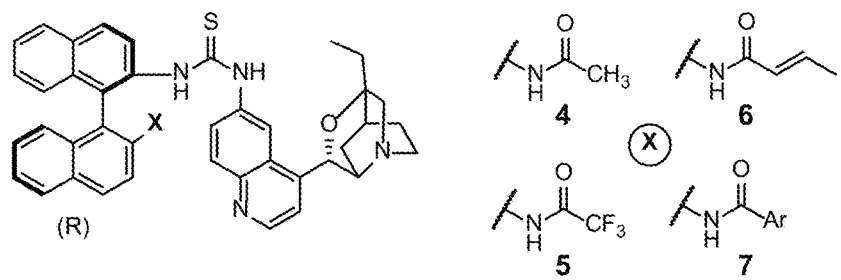
Figure 6:
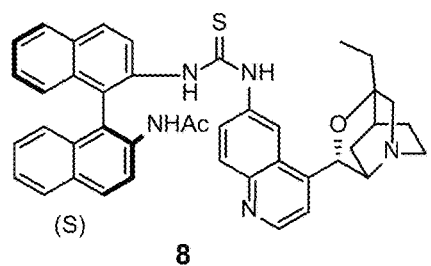

While both β-ICD and cupreidine (CPD) are effective for partial kinetic resolution of rac-LA (runs 1 and 2, Table 1), their methylated derivatives β-IQD and QD had no activity for ROP of rac-LA, which reveals the phenol OH in β-ICD and CPD is crucial as an H-bonding donor in this bifunctional catalysis. Replacing the OH group in β-ICD with a thiourea group, a double H-bonding donor, furnished catalyst 1 (FIG. 6), which significantly enhanced not only the ROP activity but also the stereoselectivity with s=10 and ee=63% at 47.8% conversion in dichloromethane (run 3). Substituting the OH group in QD and quinine (QN) with the thiourea group gave the corresponding pseudo-enantiomers 2 and 3; although this substitution turned on the ROP activity of the inactive QD and QN precursors, the stereoselectivity of 2 and 3 (runs 4 and 5) was inferior to 1, β-ICD, or CPD.

The observed much improved activity and stereoselectivity by 1 pointed us in the right direction for developing better catalysts based on derivatizing β-ICD. To this end, we reasoned that introduction of a chiral double H-bonding donor based on the binaphthyl-amine (BINAM) framework should exert double stereodifferentiation due to asymmetric activation of both the monomer (by the chiral acid) and the propagating P—OH species (by the chiral amine). It has recently been reported that a BINOL-based phosphoric acid achieved a high s factor of $k_D/k_L=28$ at 49% monomer conversion (Makiguchi et al., *Chem. Commun.* 2014, 50, 2883-2885). Accordingly, we designed and synthesized new catalyst 4, which combines three essential elements (β-ICD core, thiourea functionality, and BINAM) into a single molecule. Indeed, 4 exhibited drastically enhanced the stereoselectivity over catalyst 1, now achieving a high s factor of 32 and 85% ee at 50.1% monomer conversion (run 6).

Lowering the catalyst loading from 2 mol % to 1 mol % increased the PLA $M_n$ to $1.03 \times 10^4$ g/mol (Đ=1.14, run 7) while maintaining similar stereoselectivity. Optimization of the reaction by using fluorobenzene (FB) as the solvent further enhanced the s factor to 41 and the ee value to 89% at 50.8% monomer conversion (run 8). When o-difluorobenzene (DFB) was used, the s factor reached the highest of 53 and the ee value of 91% at 50.6% monomer conversion (run 9). Changing the X group on the BINAM from —NHAc (4) to —NHCOCF$_3$ (5), —NHCOCH=CHMe (6), and

TABLE 1

Kinetic Resolution Polymerization of Rac-LA at 25° C. by Chiral Organic Catalysts [a]

| Run # | Cat. | Solvent (rac-LA conc.) | [M]/[Cat]/[I] | Time (h) | Conv [b] (%) | ee [c] (%) | $k_S/k_R$ [d] (s) | $M_n$ [e] (kg/mol) | Đ [e] ($M_w/M_n$) |
|---|---|---|---|---|---|---|---|---|---|
| 1 | β-ICD | DCM (1.67M) | 50/1/1 | 6 | 47.6 | 40 | 3.8 | 5.53 | 1.14 |
| 2 | CPD | DCM (1.67M) | 50/1/1 | 131 | 42.4 | 33 | 3.6 | 5.37 | 1.14 |
| 3 | 1 | DCM (1.67M) | 100/1/1 | 7 | 47.8 | 63 | 10 | 11.3 | 1.13 |
| 4 | 2 | DCM (1.67M) | 50/1/1 | 36 | 53.5 | 25 | 1.9 | 6.72 | 1.10 |
| 5 | 3 | DCM (1.67M) | 50/1/1 | 22 | 52.4 | −33 [f] | 0.4 | 6.88 | 1.11 |
| 6 | 4 | DCM (1.67M) | 50/1/1 | 7 | 50.1 | 85 | 32 | 6.38 | 1.16 |
| 7 | 4 | DCM (1.67M) | 100/1/1 | 25 | 50.2 | 83 | 26 | 10.3 | 1.14 |
| 8 | 4 | FB (0.31M) | 50/1/1 | 30 | 50.8 | 89 | 41 | 6.10 | 1.12 |
| 9 | 4 | DFB (0.31M) | 50/1/1 | 17 | 50.6 | 91 | 53 | 7.21 | 1.14 |
| 10 | 4 | DFB (0.31M) | 100/1/1 | 43 | 50.5 | 88 | 38 | 11.0 | 1.12 |
| 11 [g] | 4 | DFB (0.31M) | 100/1/1 | 40 | 51.0 | 88 | 35 | 10.4 | 1.13 |
| 12 | 5 | DCM (1.67M) | 100/1/1 | 18 | 49.5 | 64 | 8.8 | 11.0 | 1.13 |
| 13 | 6 | DCM (1.67M) | 100/1/1 | 48 | 51.0 | 67 | 9.0 | 10.9 | 1.15 |
| 14 | 7 | DCM (1.67M) | 100/1/1 | 29 | 48.8 | 64 | 9.7 | 10.0 | 1.12 |
| 15 | 8 | DCM (1.67M) | 100/1/1 | 18 | 49.0 | −24 [f] | 0.5 | 11.1 | 1.13 |

[a] Carried out at 25° C. unless indicated otherwise, using BnOH as initiator (I), in dichloromethane (DCM), toluene (TOL), fluorobenzene (FB), or o-difluorobenzene (DFB).
[b] Determined by $^1$H NMR in CDCl$_3$. [c] Enantiomeric excess of the unreacted monomer measured by chiral HPLC.
[d] Calculated from $\{\ln[(1-\text{conv.})(1-\text{ee})]\}/\{\ln[(1-\text{conv.})(1+\text{ee})]\}$.
[e] Number-average molecular weight (Mn) and polydispersity index (Đ = Mw/Mn) determined by gel-permeation chromatography (GPC) at 40° C. in DMF relative to poly(methyl methacrylate) (PMMA) standards.
[f] L-LA was left.
[g] One-Pot reaction from meso-LA.

a Carried out at 25° C. unless indicated otherwise, using BnOH as initiator (I), in dichloromethane (DCM), toluene (TOL), fluorobenzene (FB), or o-difluorobenzene (DFB). b Determined by $^1$H NMR in CDCl$_3$. c Enantiomeric excess of the unreacted monomer measured by chiral HPLC. d Calculated from $\{\ln [(1-\text{conv.})(1-\text{ee})]\}/\{\ln [(1-\text{conv.})(1+\text{ee})]\}$. e Number-average molecular weight (Mn) and polydispersity index (D=Mw/Mn) determined by gel-permeation chromatography (GPC) at 40° C. in DMF relative to poly(methyl methacrylate) (PMMA) standards. f L-LA was left. g One-Pot reaction from meso-LA.

—NHCOAr (7, Ar=4-CF$_3$C$_6$H$_4$) drastically reduced catalyst stereoselectivity (runs 12-14). Flipping the BINAM from R to S (8) yielded a much inferior catalyst (run 15).

Figure 2:
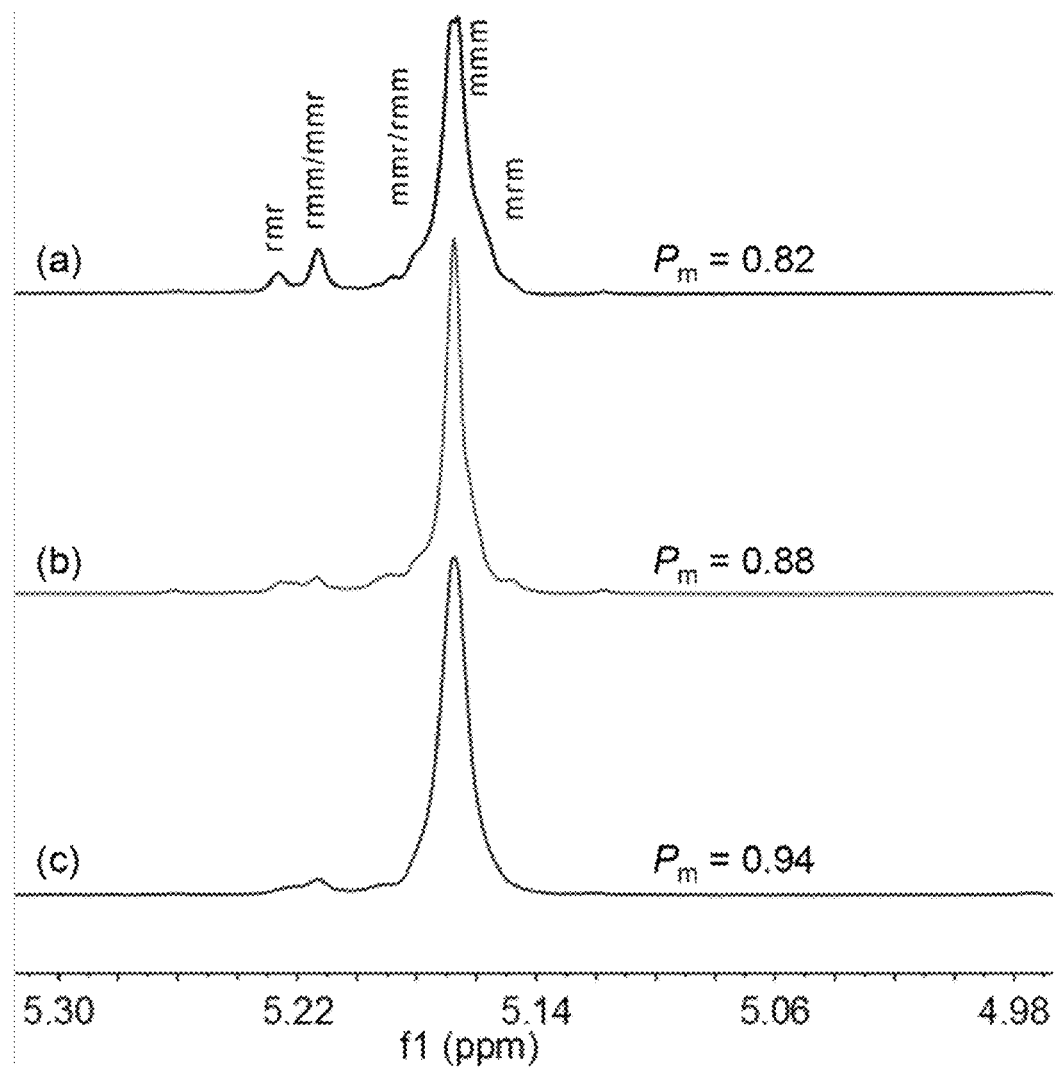
FIG. 2. Homonuclear decoupled $^1$H NMR spectra (400 MHz, CDCl$_3$) of the methane region of PLAs from rac-LA: (a) catalyst 4, 25° C., 82.9% conversion; (b) catalyst 4, 25° C., 50.5% conversion; (c) $^t$Bu-P$_2$, −75° C., >99% conversion.

With both tasks now having been met, we set out to examine the possibility of carrying out meso-LA to rac-LA epimerization and enantioselective polymerization in a one-pot fashion. We first confirmed that the isolated rac-LA from the epimerization reaction was polymerized into it-PLA ($P_m$=0.94, at −75° C., FIG. 2), the result of which is nearly identical to the ROP of rac-LA ($P_m$=0.95, at −75° C., or $P_m=0.72$, at 20° C.) reported in the literature (Zhang et al., J. Am. Chem. Soc. 2007, 129, 12610-12611), using the same catalyst phosphazene $^t$Bu-$P_2$. In comparison, the chiral catalyst 4 produced it-PLA with a higher $P_m$ value of 0.82 at 25° C. (the ee of the unreacted monomer was 99%). Finally, we first performed the quantitative epimerization of meso-LA (0.721 g) by DABCO/B($C_6F_5$)$_3$ (0.01 mol %) in toluene, removed the solvent to give rac-LA/meso-LA in a ratio of 99/1, and then added catalyst 4 in DFB for subsequent kinetic resolution polymerization. The results were similar (only with a slightly lower s value, run 11 vs. 10) to those obtained using the pure rac-LA under the same reaction conditions.

In conclusion, we have discovered that the Lewis pair DABCO/B($C_6F_5$)$_3$ catalyzes rapid and quantitative epimerization of meso-LA, often regarded as a "waste" side-product of the L-LA production process, into rac-LA. The keys for achieving quantitative conversion of this isomerization process include (a) a highly effective LP catalyst system that enables the rapid epimerization at ambient temperature, under which conditions the equilibrium is shifted further towards rac-LA and LA oligomerization can also be avoided; and (b) continuous removal of the formed rac-LA from the reaction mixture through precipitation of rac-LA from solution due to solubility differences. This epimerization method can convert LA stereoisomers in any ratio into essentially pure rac-LA (Table A). We also developed a highly enantioselective bifunctional chiral organic catalyst that incorporates three essential elements (β-ICD core, thiourea functionality, and BINAM) into a single molecule. Using this catalyst, rac-LA is polymerized enantioselectively into it-PLLA and optically resolved D-LA with a high stereoselectivity factor of 53 and the ee value of 91% at 50.6% monomer conversion. The epimerization and kinetic resolution polymerization can be coupled into a one-pot process, effectively transforming meso-LA directly into it-PLLA and D-LA. The results reported herein expand the catalytic utility of the two emerging frontiers: the FLP chemistry and organocatalytic polymerization.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials and Reagents.

All syntheses and manipulations of air- and moisture-sensitive materials were carried out in flamed Schlenk-type glassware on a dual-manifold Schlenk line, on a high-vacuum line, or in an inert gas (Ar or $N_2$)-filled glovebox. HPLC-grade organic solvents were first sparged extensively with nitrogen during filling 20 L solvent reservoirs and then dried by passage through activated alumina (for $Et_2O$, THF, and $CH_2Cl_2$) followed by passage through Q-5 supported copper catalyst (for toluene and hexanes) stainless steel columns. HPLC-grade dimethylformamide (DMF) was degassed and dried over $CaH_2$ overnight, followed by vacuum distillation ($CaH_2$ was removed before distillation). Toluene-$d_8$ was dried over sodium/potassium alloy and vacuum-distilled or filtered, whereas $CD_2Cl_2$ and $CDCl_3$ were distilled over $CaH_2$ and then stored over activated Davison 4 Å molecular sieves. NMR spectra were recorded on Varian Inova 400 MHz (FT 400 MHz, $^1H$; 100 MHz, $^{13}C$; 376 MHz, $^{19}F$) and 500 MHz spectrometers. Chemical shifts for all spectra were referenced to internal solvent resonances and were reported as parts per million relative to $SiMe_4$.

L-Lactide (L-LA), rac-lactide (rac-LA), 1,4-diazabicyclo[2.2.2]octane (DABCO), and benzyl alcohol (BnOH) were purchased from Sigma-Aldrich. BnOH was distilled over $CaH_2$ and then stored over activated Davison 4 Å molecular sieves. The lactide monomers and DABCO were purified by sublimation. Meso-lactide (meso-LA) was obtained as a research gift from NatureWorks Co. and further purified by recrystallizations from dry toluene and double sublimation under vacuum. Tris(pentafluorophenyl)borane, B($C_6F_5$)$_3$, was obtained as a research gift from Boulder Scientific Co. and further purified by double sublimation under vacuum. Cinchonidine (CD), cinchonine (CN), quinine (QN), quinidine (QD), β-isocupreidine (β-ICD) were purchased from TCI America and used as received. Other commercial reagents were purchased from Sigma-Aldrich and used as received.

Example 1. Preparation of Compounds and Catalysts

1. Preparation of β-Isoquinidine (β-IQD).

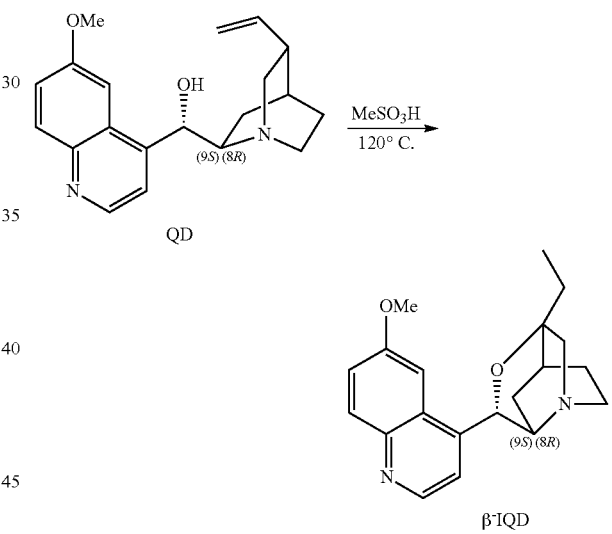

A solution of quinidine (2.0 g, 6.2 mmol) in methanesulfonic acid (20 ml) was heated to 120° C. for 1 h. The solution was cooled down to 0° C. and added dropwise to 20% KOH solution slowly till pH≈10 was reached and colorless precipitates were formed. The mixture was extracted with chloroform, and the organic layer was collected, dried over anhydrous $Na_2SO_4$. The solution was filtered and concentrated under reduced pressure. The residue was purified by column chromatography on silica gel (EtOAc/MeOH/$NH_3.H_2O$=100/1/1) to give the titled compound β-IQD (Waldmann et al., Angew. Chem. Int. Ed. 2008, 47, 6869-6872) (44% yield) as white foam. $^1H$ NMR (400 MHz, $CDCl_3$, TMS): δ 8.77 (d, J=4.8 Hz, 1H), 8.01 (d, J=9.2 Hz, 1H), 7.72 (d, J=3.6 Hz, 1H), 7.34 (dd, J=9.2, 2.8 Hz, 1H), 7.14 (d, J=3.2 Hz, 1H), 5.92 (s, 1H), 3.94 (s, 3H), 3.52 (d, J=13.2 Hz, 1H), 3.46 (d, J=6.0 Hz, 1H), 3.00-2.97 (m, 2H), 2.65 (d, J=13.2 Hz, 1H), 2.14-2.11 (m, 1H), 1.78-1.73 (m, 1H), 1.70-1.62 (m, 3H), 1.53-1.46 (m, 1H), 1.27-1.22 (m, 1H), 1.02 (t, J=7.6 Hz, 3H).

2. Preparation of Cupreidine (CPD).

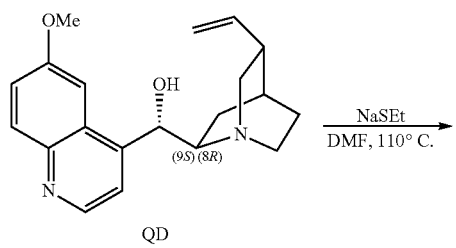

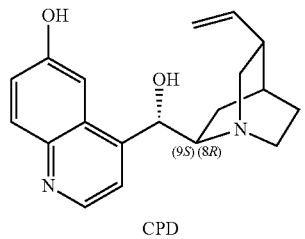

Under N$_2$ atmosphere, a suspension of quinidine (0.20 g, 0.62 mmol) and NaSEt (0.21 g, 2.48 mmol) in dry DMF (6 ml) was stirred at 110° C. until a TLC analysis showed that the starting material was completely consumed (4 h). The reaction mixture was cooled down to room temperature, mixed with saturated NH$_4$Cl aqueous solution. The pH value of the solution was determined to be around 7. The resulting mixture was extracted with EtOAc, and the organic layer was collected, dried over anhydrous Na$_2$SO$_4$. The solution was filtered and concentrated under reduced pressure. The residue was purified by column chromatography on silica gel (EtOAc/MeOH/NH$_3$.H$_2$O=100/6/1) to give the compound CPD (Li et al., *J. Am. Chem. Soc.* 2004, 126, 9906-9907) (77% yield) as pale yellow foam. $^1$H NMR (400 MHz, DMSO-d$_6$, TMS): δ 10.04 (brs, 1H), 8.64 (d, J=4.4 Hz, 1H), 7.89 (d, J=9.6 Hz, 1H), 7.46-7.48 (m, 2H), 7.31 (dd, J=9.2 and 2.4 Hz, 1H), 6.16-6.07 (m, 1H), 5.68 (brs, 1H), 5.21-5.10 (m, 3H), 3.14-3.03 (m, 2H), 2.78-2.60 (m, 3H), 2.27-2.21 (m, 1H), 1.97-1.91 (m, 1H), 1.73 (s, 1H), 1.56-1.36 (m, 3H).

3. Preparation of Thiocarbamate-QD.

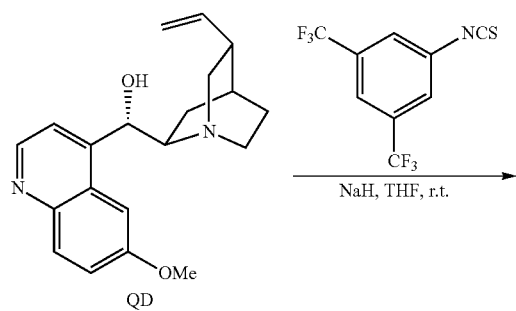

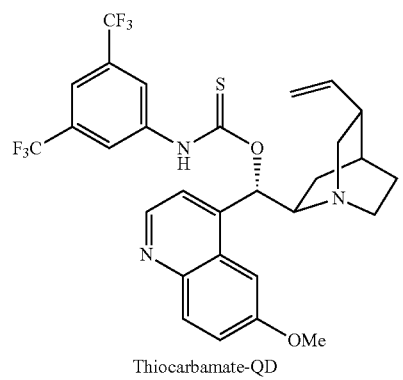

To a solution of quinidine (649 mg, 2.0 mmol) and 3,5-bis(trifluoromethyl)phenyl isothiocyanate (612 mg, 2.4 mmol) in THF (10 mL) was added sodium hydride (160 mg, 4.0 mmol, 60% in mineral oil). The reaction was stirred at room temperature until a TLC analysis showed that the starting material was completely consumed (15 h). The reaction was quenched with water (20 ml) and extracted with dichloromethane. The combined organic extracts were washed with brine (10 ml), dried over anhydrous Na$_2$SO$_4$, filtrated, and concentrated in vacuo. The residue was purified by flash column chromatography (EtOAc/MeOH/NH$_3$.H$_2$O=10/2/1) to give the titled compound thiocarbamate-QD (Zhou et al., *J. Am. Chem. Soc.* 2010, 132, 15474-15476) (75% yield) as a pale yellow solid. $^1$H NMR (400 MHz, CDCl$_3$, TMS): δ 8.92-8.25 (brs, 1H), 8.73 (d, J=4.4 Hz, 1H), 8.01-7.85 (m, 3H), 7.69 (s, 1H), 7.58 (d, J=3.2 Hz, 1H), 7.38-7.34 (m, 2H), 7.30 (d, J=4.8 Hz, 1H), 6.06-5.98 (m, 1H), 5.12-5.08 (m, 2H), 3.93 (s, 3H), 3.50-3.43 (m, 1H), 2.90 (d, J=8.4 Hz, 2H), 2.80-2.65 (m, 2H), 2.31-2.25 (1H), 1.98-1.96 (m, 1H), 1.84 (brs, 1H), 1.68-1.54 (m, 3H).

4. Preparation of Catalyst 1.

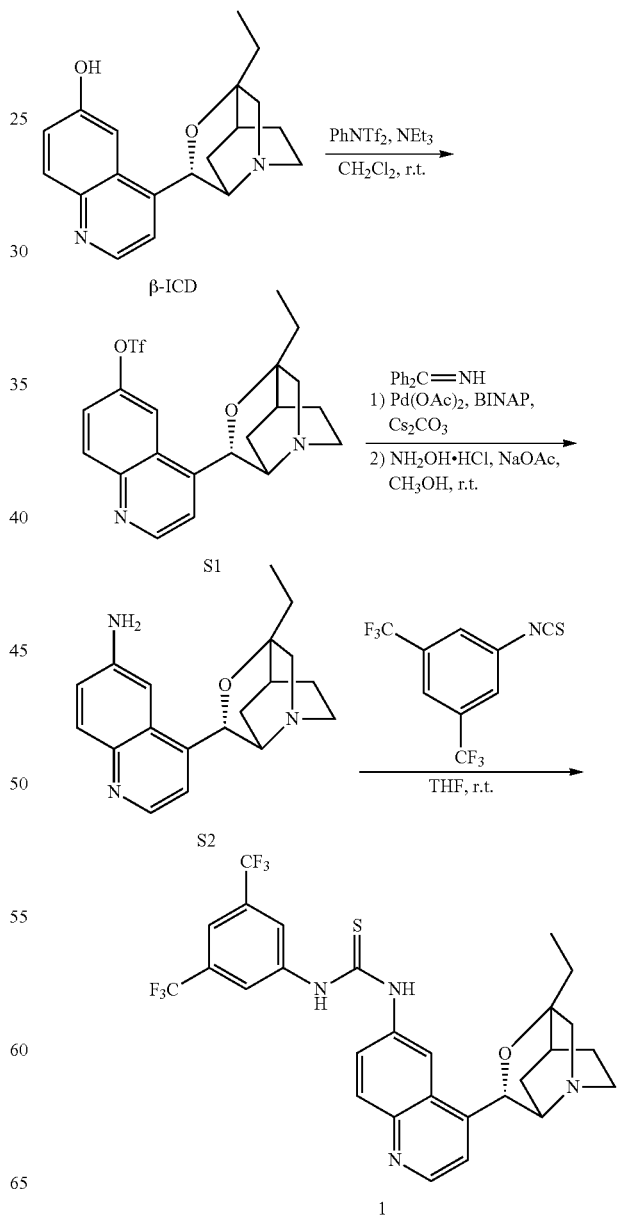

To a solution of β-ICD (2.48 g, 8.0 mmol) and N-phenylbis(trifluoromethane-sulfonimide) (3.43 g, 9.6 mmol) in anhydrous methylene chloride (60 mL) was added triethylamine (2.02 g, 20 mmol) at room temperature. After the completion of the reaction (monitored by TLC, in 12 h), the reaction mixture was transferred to a separation funnel, washed with saturated sodium carbonate aqueous solution and brine, the organic layer was collected, dried over anhydrous $Na_2SO_4$. The solution was filtered and concentrated under reduced pressure. The residue was purified by column chromatography on silica gel (EtOAc/MeOH/$NH_3$.$H_2O$=100/3/1) to give product S1 (98% yield) as white foam. $^1$H NMR (400 MHz, $CDCl_3$, TMS): δ 9.00 (d, J=4.4 Hz, 1H), 8.23 (d, J=9.2 Hz, 1H), 7.92 (d, J=6.8 Hz, 1H), 7.83 (dd, J=4.4, 0.8 Hz, 1H), 7.61 (dd, J=9.2, 2.4 Hz, 1H), 5.93 (s, 1H), 3.54 (d, J=13.6 Hz, 1H), 3.42 (d, J=6.4 Hz, 1H), 3.03-3.00 (m, 2H), 2.70 (d, J=13.2 Hz, 1H), 2.15-2.13 (m, 1H), 1.74-1.63 (m, 4H), 1.55-1.49 (m, 1H), 1.32-1.28 (m, 1H), 1.03 (t, J=7.6 Hz, 3H).

S1 (1.3 g, 2.94 mmol), palladium acetate (132 mg, 0.58 mmol), BINAP (183 mg, 0.294 mmol), $Cs_2CO_3$ (1.15 g, 3.53 mmol), and benzophenone imine (1.1 g, 5.88 mmol) were suspended in THF (40 mL). The reaction mixture was refluxed with stirring for 12 h. After the completion of the reaction (monitored by TLC), the reaction mixture was cooled to room temperature, diluted with EtOAc, washed with 5% sodium carbonate aqueous solution and brine. The organic layer was collected, dried over anhydrous sodium sulfate and concentrated under reduced pressure to get crude imine that was used directly for the next step without further purification. To the solution of the residue (1.24 g) in methanol (30 mL), was added $NH_2OH.HCl$ (408.7 mg, 5.88 mmol) and NaOAc (723 mg, 8.82 mmol). After the completion of the reaction (monitored by TLC, in 3 h), the reaction mixture was concentrated and extracted with saturated $Na_2CO_3$ (aq.) and $CH_2Cl_2$. The organic layers were collected, washed with brine, dried over anhydrous sodium sulfate. The solution was filtered and concentrated under reduced pressure. The residue was purified by column chromatography on silica gel (EtOAc/MeOH/$NH_3.H_2O$=100/5/2) to give product S2 (68% yield) as yellow foam. $^1$H NMR (400 MHz, $CDCl_3$, TMS): δ 8.59 (d, J=4.8 Hz, 1H), 7.93 (d, J=9.2 Hz, 1H), 7.57 (d, J=4.4 Hz, 1H), 7.03 (dd, J=9.2 and 2.0 Hz, 1H), 6.90 (d, J=2.0 Hz, 1H), 5.79 (s, 1H), 4.03 (s, 2H), 3.47-3.38 (m, 2H), 2.93-2.90 (m, 2H), 2.58 (d, J=13.6 Hz, 1H), 2.05-2.03 (m, 1H), 1.71-1.66 (m, 1H), 1.60-1.54 (m, 3H), 1.44-1.38 (m, 1H), 1.18-1.14 (m, 1H), 0.95 (t, J=7.8 Hz, 3H).

To a solution of S2 (480 mg, 1.55 mmol) in THF (15 mL) was added 3,5-bis-trifluoromethylphenyl isothiocyanate (475 mg, 1.86 mmol) and the reaction mixture was stirred for 12 h at room temperature. The reaction mixture was concentrated and the crude product was purified by flash chromatograph on silica gel (EtOAc/MeOH/$NH_3.H_2O$=100/3/1) to give catalyst 1 (Song et al., J Am. Chem. Soc. 2006, 128, 6048-6049)(82% yield) as a pale yellow solid. $^1$H NMR (400 MHz, DMSO-$d_6$, TMS): δ 10.50 (brs, 2H), 8.90 (d, J=4.4 Hz, 1H), 8.32 (s, 2H), 8.07-8.05 (m, 2H), 7.93-7.90 (m, 1H), 7.81 (s, 1H), 7.71 (d, J=4.4 Hz, 1H), 5.92 (s, 1H), 3.52-3.44 (m, 2H), 2.92-2.83 (m, 2H), 2.76-2.23 (m, 1H), 2.10 (brs, 1H), 1.70-1.58 (m, 4H), 1.46-1.44 (m, 1H), 1.32-1.30 (m, 1H), 0.99 (t, J=7.6 Hz, 3H).

5. Preparation of Catalysts 2 and 3.

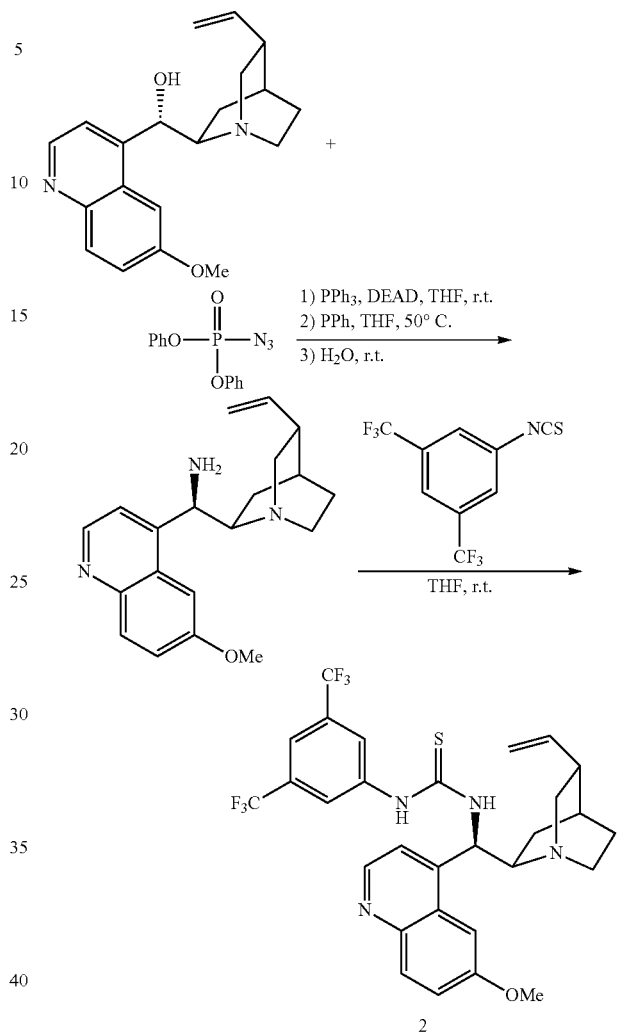

Quinidine (1.62 g, 5.0 mmol) and triphenylphosphine (1.6 g, 6.0 mmol) were dissolved in THF (25 mL), and the solution was cooled to 0° C. Diethyl azodicarboxylate (1.0 g, 6.0 mmol) was subsequently added in one portion. Then a solution of diphenyl phosphoryl azide (1.3 mL, 6 mmol) in THF (10 mL) was added dropwise at 0° C. The mixture was allowed to warm to ambient temperature. After being stirred for 24 h, it was heated to 50° C. and stirred for 17 h. The reaction mixture was cooled to room temperature. Triphenylphosphine (1.7 g, 6.5 mmol) was added again, and the mixture was stirred at 50° C. for additional 15 h. After the solution was cooled to ambient temperature, $H_2O$ (0.5 mL) was added, and the solution was stirred for 24 h. After the solvents were removed in vacuo, the residue was dissolved in $CH_2Cl_2$ and 10% hydrochloric acid (25 mL/25 mL). The aqueous phase was washed with $CH_2Cl_2$ (4×25 mL). It was subsequently made alkaline with aqueous ammonia, and the aqueous phase was extracted with $CH_2Cl_2$, and the organic layer was collected, dried over anhydrous $Na_2SO_4$. The solution was filtered and concentrated under reduced pressure. The residue was purified by column chromatography on silica gel (EtOAc/MeOH/$NH_3.H_2O$=50/3/1) to give product 9-amino(9-deoxy)cinchona alkaloid as pale yellow foam. Next, to the solution of the obtained 9-amino(9-deoxy)cinchona alkaloid (324 mg, 1.0 mmol) in THF (4 mL) was slowly added a solution of 3,5-bis(trifluoromethyl)phenyl isothiocyanate (298 mg, 1.1 mmol) in THF (2 mL) at ambient temperature. The mixture was stirred overnight, and the solvents were removed in vacuo. The residue was purified by column chromatography on silica gel (EtOAc/MeOH/NH$_3$·H$_2$O=500/5/1) to give product 2 (Fukata et al., *J. Am. Chem. Soc.* 2013, 135, 12160-12163) as a white solid. $^1$H NMR (400 MHz, DMSO-d$_6$, TMS): δ 10.17 (brs, 1H), 8.89 (d, J=6.4 Hz, 1H), 8.69 (d, J=4.4 Hz, 1H), 8.10 (s, 2H), 7.89 (d, J=9.2 Hz, 1H), 7.85 (s, 1H), 7.65 (s, 1H), 7.57 (d, J=4.8 Hz, 1H), 7.38 (dd, J=10.8, 2.8 Hz, 1H), 6.04 (brs, 1H), 5.96-5.88 (m, 1H), 5.17-5.08 (m, 2H), 3.92 (s, 3H), 3.28-3.19 (m, 1H), 3.08-3.01 (m, 1H), 2.93-2.82 (m, 3H), 2.28-2.22 (m, 1H), 1.54-1.42 (m, 3H), 1.08-1.03 (m, 1H), 0.88-0.77 (m, 1H).

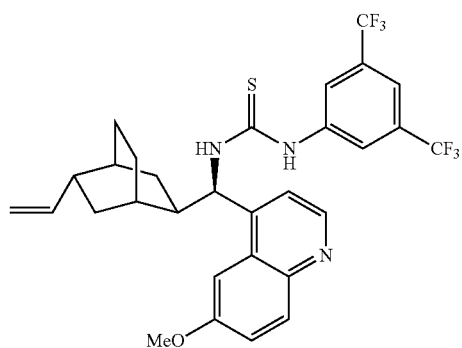

3

Catalyst 3 (Fukata et al., *J. Am. Chem. Soc.* 2013, 135, 12160-12163), white solid; 34% yield for 2 steps from quinine. $^1$H NMR (400 MHz, DMSO-d$_6$, TMS): δ 10.28 (brs, 1H), 9.00 (d, J=6.4 Hz, 1H), 8.78 (d, J=4.0 Hz, 1H), 8.19 (s, 2H), 8.00-7.98 (m, 2H), 7.73 (s, 1H), 7.66 (d, J=4.4 Hz, 1H), 7.48 (dd, J=9.6, 2.8 Hz, 1H), 6.10 (brs, 1H), 5.91-5.82 (m, 1H), 5.06-4.96 (m, 2H), 4.00 (s, 3H), 3.36-3.22 (m, 3H), 2.77 (brs, 2H), 2.32 (brs, 1H), 1.72-1.54 (m, 3H), 1.34-1.23 (m, 1H), 0.90-0.80 (m, 1H).

6. Synthesis of Catalysts 4-8.

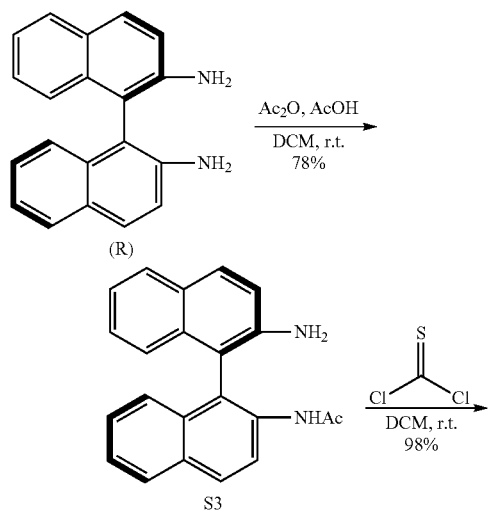

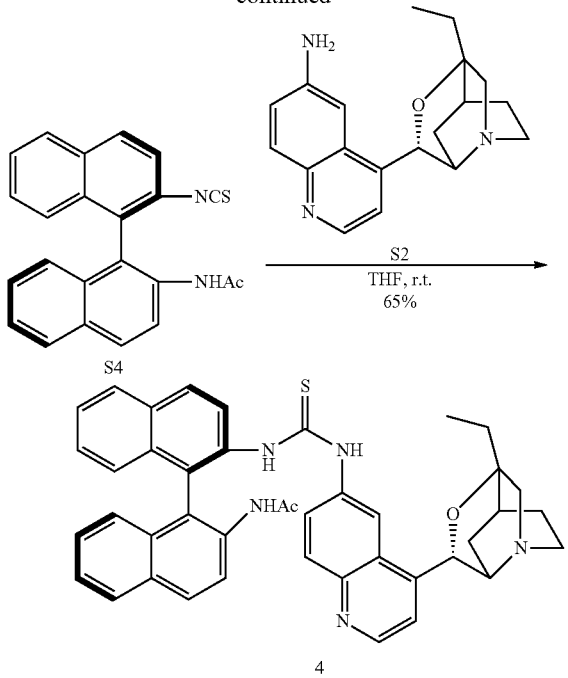

To a solution of (R)-(+)-1,1'-binaphthyl-2,2'-diamine (2.84 g, 10 mmol) and AcOH (6 mL, 100 mmol) in 80 mL of dried CH$_2$Cl$_2$ was added acetic anhydride (1 mL, 10 mmol) at 0° C. under N$_2$. The resulting solution was stirred for overnight at room temperature, and 2N NaOH aqueous solution was added to adjust the solution to pH≈17. The reaction mixture was extracted with CH$_2$Cl$_2$ and the combined organic phases were washed with saturated brine and dried over anhydrous Na$_2$SO$_4$. The solution was filtered and concentrated under reduced pressure. The residue was purified by column chromatography on silica gel (hexane/EtOAc=3/2) to give product S3 (Wang et al., *Org. Lett.* 2005, 7, 4713-4716) (78% yield) as a white solid. $^1$H NMR (400 MHz, CDCl$_3$, TMS): δ 8.63 (d, J=8.8 Hz, 1H), 8.00 (d, J=9.2 Hz, 1H), 7.91 (d, J=8.0 Hz, 1H), 7.86 (d, J=8.8 Hz, 1H), 7.82 (d, J=7.6 Hz, 1H), 7.43-7.39 (m, 1H), 7.28-7.14 (m, 5H), 7.02 (s, 1H), 6.92 (d, J=8.0 Hz, 1H), 3.66 (s, 2H), 1.86 (s, 3H).

A literature procedure (Burns et al., *J. Am. Chem. Soc.* 2011, 133, 14578-14581) was modified for the preparation of compound S4. S3 (326 mg, 1.0 mmol) was dissolved in CH$_2$Cl$_2$ (6 mL) and sat. aq. NaHCO$_3$ (6 mL) was added. The resulting biphasic solution was cooled to 0° C. and thiophosgene (0.1 mL, 1.3 mmol, 1.3 equiv) was then carefully added. The reaction was allowed to warm to room temperature and stirred for 12 h. The layers were separated and the aqueous layer was extracted with CH$_2$Cl$_2$. The organic layers were collected, washed with brine, dried over anhydrous sodium sulfate. The solution was filtered and concentrated under reduced pressure to get pure product S4 (98% yield) as a pale yellow solid, which was used directly in the subsequent reaction without further purification. $^1$H NMR (400 MHz, CDCl$_3$, TMS): δ 8.48 (d, J=8.4 Hz, 1H), 7.99-7.85 (m, 4H), 7.49-7.28 (m, 4H), 7.23-7.15 (m, 2H), 6.90 (d, J=8.4 Hz, 1H), 6.57 (m, 1H), 1.75 (s, 3H).

To a solution of S2 (61.9 mg, 0.2 mmol) in THF (5 mL) was added S4 (88.4 mg, 0.24 mmol) and the reaction mixture was stirred for 17 h at room temperature. The reaction mixture was concentrated and the crude product was purified by flash chromatograph on silica gel (EtOAc/MeOH/NH$_3$·H$_2$O=100/3/1) to give catalyst 4 (65% yield) as a pale yellow solid. $[\alpha]_D^{24}=213.2°$ (c=0.167 g/100 mL, $CH_2Cl_2$); $^1H$ NMR (400 MHz, $CDCl_3$, TMS): δ 10.9 (brs, 1H), 8.88 (d, J=4.0 Hz, 1H), 8.87 (brs, 1H), 7.97 (d, J=9.2 Hz, 1H), 7.90 (d, J=8.0 Hz, 1H), 7.84 (brs, 2H), 7.70 (d, J=4.4 Hz, 1H), 7.59-7.53 (m, 2H), 7.48 (s, 1H), 7.42-7.35 (m, 2H), 7.21-7.12 (m, 3H), 6.99 (t, J=8.0 Hz, 1H), 6.92 (d, J=8.4 Hz, 1H), 6.75 (d, J=8.4 Hz, 1H), 6.50 (brs, 1H), 5.84 (s, 1H), 3.69-3.66 (m, 1H), 2.86-2.85 (m, 1H), 2.69 (brs, 1H), 2.51 (d, J=13.6 Hz, 1H), 2.34 (s, 1H), 2.09-2.04 (m, 1H), 1.76 (s, 3H), 1.59-1.47 (m, 4H), 1.32-1.21 (m, 1H), 0.95 (t, J=7.2 Hz, 3H), 0.89-0.79 (m, 1H); $^{13}C$ NMR (100 MHz, $CDCl_3$): δ 179.2, 168.8, 150.6, 146.0, 144.8, 136.4, 135.5, 134.3, 132.2, 131.8(1), 131.7(6), 131.6, 130.5, 128.9, 128.7, 128.3, 128.0, 127.0, 126.8, 126.1, 125.8, 125.5, 125.3, 125.1, 125.0, 124.2, 122.4, 119.8, 118.4, 77.1, 72.6, 56.5, 54.4, 46.8, 33.0, 27.4, 24.2, 23.7, 23.4, 7.3; IR v/cm$^{-1}$ 3239 (brs), 2932 (m), 1668 (m), 1594 (m), 1498 (m), 1274 (m), 908 (m), 817 (m), 726 (m); HRMS (positive ESI) calcd for $C_{42}H_{410}N_5O_2S^{+1}$ ([M+H]$^+$): 678.2897; found: 678.2903.

To a solution of (R)-(+)-1,1'-binaphthyl-2,2'-diamine (0.5 g, 1.76 mmol) and $CF_3CO_2H$ (1.5 mL) in 15 mL of dried $CH_2Cl_2$ was added $(CF_3CO)_2O$ (0.25 mL, 1.76 mmol) at 0° C. under $N_2$. The resulting solution was stirred for overnight at room temperature, and 2N NaOH aqueous solution was added to adjust the solution to pH≈7. The reaction mixture was extracted with $CH_2Cl_2$ and the combined organic phases were washed with saturated brine and dried over anhydrous $Na_2SO_4$. The solution was filtered and concentrated under reduced pressure. The residue was purified by column chromatography on silica gel (hexane/EtOAc=25/1) to give product S5 (71% yield) as a white solid. $^1H$ NMR (400 MHz, $CDCl_3$, TMS): δ 8.54 (d, J=9.0 Hz, 1H), 8.05 (d, J=9.0 Hz, 1H), 7.94 (d, J=8.2 Hz, 1H), 7.90 (s, 1H), 7.87 (d, J=8.8 Hz, 1H), 7.81 (d, J=8.8 Hz, 1H), 7.50-7.46 (m, 1H), 7.35-7.17 (m, 4H), 7.13 (d, J=8.2 Hz, 1H), 6.86-6.81 (m, 1H), 3.65 (s, 2H).

S5 (270 mg, 0.64 mmol) was dissolved in $CH_2Cl_2$ (6 mL) and sat. aq. $NaHCO_3$ (6 mL) was added. The resulting biphasic solution was cooled to 0° C. and thiophosgene (0.06 mL, 0.83 mmol, 1.3 equiv) was then carefully added. The reaction was allowed to warm to room temperature and stirred for 12 h. The layers were separated and the aqueous layer was extracted with $CH_2Cl_2$. The organic layers were collected, washed with brine, dried over anhydrous sodium sulfate. The solution was filtered and concentrated under reduced pressure to get pure product S6 (95% yield) as a pale yellow solid, which was used directly in the subsequent reaction without further purification. $^1H$ NMR (400 MHz, $CDCl_3$, TMS): δ 8.49 (d, J=9.0 Hz, 1H), 8.14 (d, J=9.0 Hz, 1H), 8.07 (d, J=8.8 Hz, 1H), 7.99 (dd, J=8.2, 3.4 Hz, 2H), 7.58-7.53 (m, 3H), 7.45-7.33 (m, 3H), 7.18 (d, J=8.5 Hz, 1H), 7.12 (d, J=8.5 Hz, 1H).

Catalyst 5 was synthesized from S2+S6 using the same procedure as that described for catalyst 4 from S2+S4, obtained as a pale yellow solid in 55% yield; $[\alpha]_D^{24}=162.9°$ (c=0.167 g/100 mL, $CH_2Cl_2$); $^1H$ NMR (400 MHz, $CDCl_3$, TMS): δ 8.96-8.83 (m, 2H), 8.53 (brs, 1H), 7.89-7.85 (m, 3H), 7.79-7.73 (m, 2H), 7.65-7.63 (m, 2H), 7.50-7.36 (m, 4H), 7.28 (t, J=7.6 Hz, 1H), 7.17 (t, J=7.2 Hz, 1H), 7.06 (t, J=8.0 Hz, 1H), 6.96-6.92 (m, 2H), 6.49 (brs, 1H), 5.75 (s, 1H), 3.58-3.55 (m, 1H), 3.08 (brs, 1H), 2.74 (brs, 1H), 2.53-2.49 (m, 2H), 2.00 (brs, 1H), 1.58-1.48 (m, 4H), 1.36-1.32 (m, 1H), 0.94-0.91 (m, 4H); $^{13}C$ NMR (100 MHz, $CDCl_3$): δ 180.0, 172.9, 155.5 (q, $J_{C-F}$=37.9 Hz), 150.4, 145.9, 144.3, 136.3, 134.6, 132.4, 132.0 (0), 131.9 (6), 131.7, 131.6, 129.6, 129.1, 128.5, 128.2, 127.4, 127.3, 126.3, 126.2, 125.9, 125.4, 124.7, 124.6, 122.8, 120.0, 117.8, 116.9, 114.0, 77.1, 72.4, 56.5, 54.2, 46.4, 32.8, 27.3, 23.4, 23.1, 7.2; IR v/cm$^{-1}$ 3239 (brs), 2961 (m), 2880 (m), 1670 (m), 1594 (m), 1500 (s), 1274 (m), 817 (m), 727 (m); HRMS (positive ESI) calcd for $C_{42}H_{37}F_3N_5O_2S^{+1}$ ([M+H]$^+$): 732.2615; Found: 732.2624.

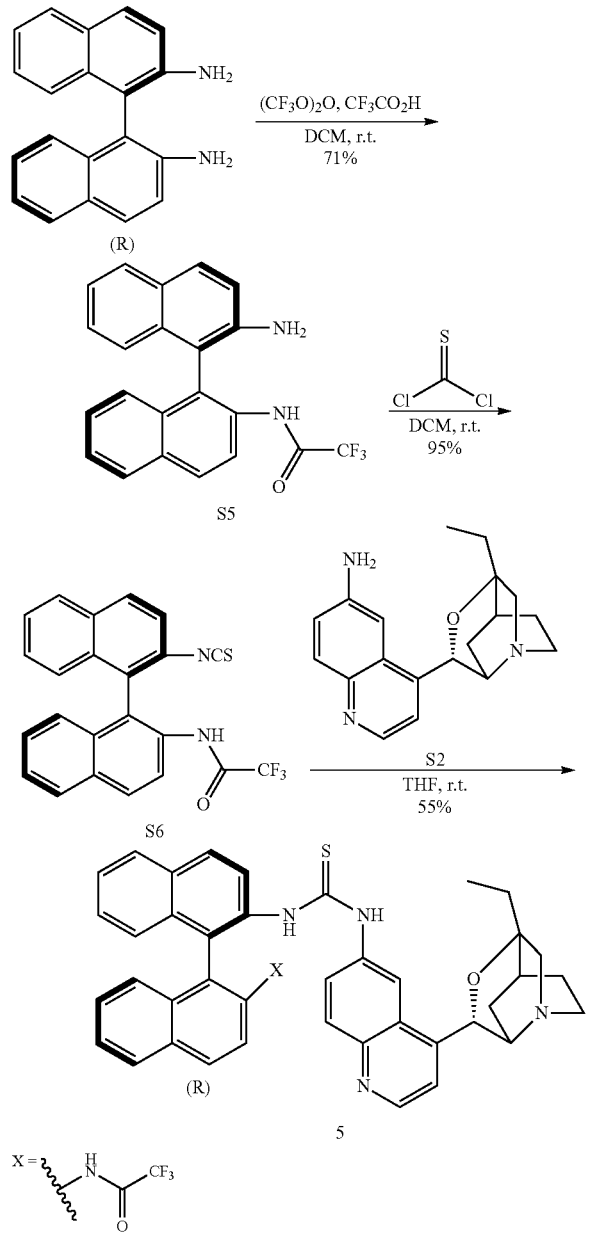

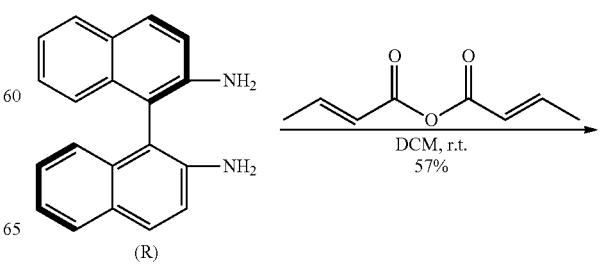

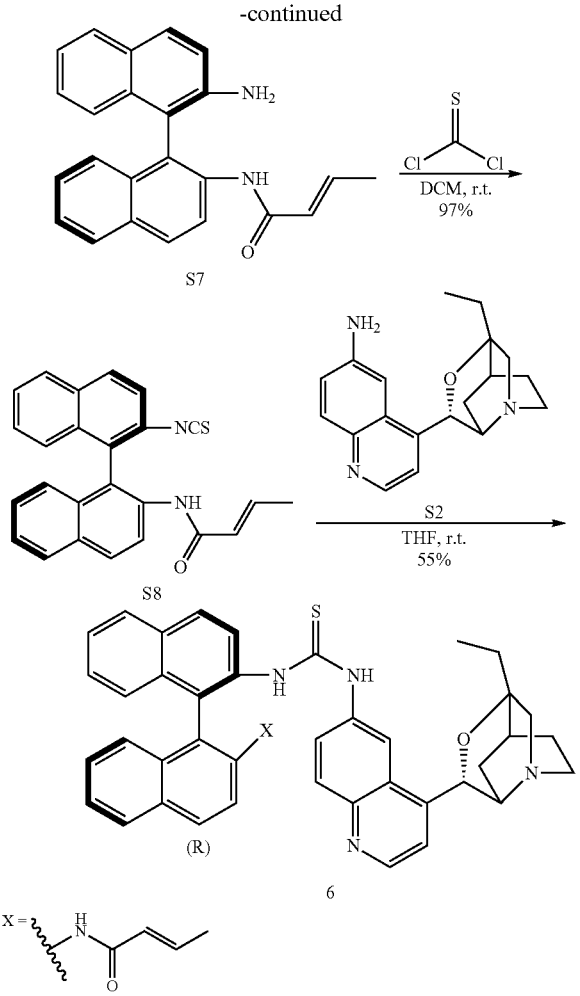

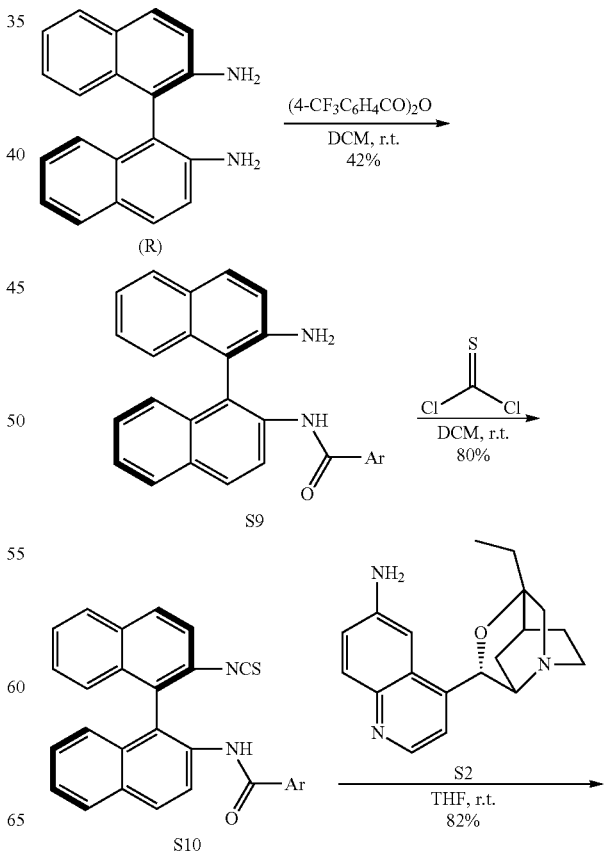

To a solution of (R)-(+)-1,1'-binaphthyl-2,2'-diamine (0.284 g, 1.0 mmol) in 15 mL of dried CH$_2$Cl$_2$ was added crotonic anhydride (0.15 mL, 1.0 mmol) at 0° C. under N$_2$. The resulting solution was stirred for overnight at room temperature, and 2N NaOH aqueous solution was added to adjust the solution to pH≈7. The reaction mixture was extracted with CH$_2$Cl$_2$ and the combined organic phases were washed with saturated brine and dried over anhydrous Na$_2$SO$_4$. The solution was filtered and concentrated under reduced pressure. The residue was purified by column chromatography on silica gel (hexane/EtOAc=10/1) to give product S7 (57% yield) as a pale yellow solid. $^1$H NMR (400 MHz, CDCl$_3$, TMS): δ 8.75 (d, J=9.1 Hz, 1H), 7.98 (d, J=9.1 Hz, 1H), 7.89 (d, J=8.2 Hz, 1H), 7.85 (d, J=8.8 Hz, 1H), 7.80 (d, J=8.0 Hz, 1H), 7.38 (ddd, J=8.1, 6.8, 1.2 Hz, 1H), 7.27-7.11 (m, 5H), 7.04 (s, 1H), 6.90 (d, J=8.3 Hz, 1H), 6.69 (dq, J=13.7, 6.9 Hz, 1H), 5.47 (d, J=15.1 Hz, 1H), 3.80 (s, 2H), 1.71 (dd, J=6.9, 1.6 Hz, 3H).

S7 (200 mg, 0.57 mmol) was dissolved in CH$_2$Cl$_2$ (6 mL) and sat. aq. NaHCO$_3$ (6 mL) was added. The resulting biphasic solution was cooled to 0° C. and thiophosgene (0.056 mL, 0.738 mmol, 1.3 equiv) was then carefully added. The reaction was allowed to warm to room temperature and stirred for 12 h. The layers were separated and the aqueous layer was extracted with CH$_2$Cl$_2$. The organic layers were collected, washed with brine, dried over anhydrous sodium sulfate. The solution was filtered and concentrated under reduced pressure to get pure product S8 (97% yield) as a pale yellow solid, which was used directly in the subsequent reaction without further purification. $^1$H NMR (400 MHz, CDCl$_3$, TMS): δ 8.64 (s, 1H), 8.02 (dd, J=12.4, 9.0 Hz, 2H), 7.93 (dd, J=12.5, 8.3 Hz, 2H), 7.55-7.44 (m, 2H), 7.41 (t, J=7.5 Hz, 1H), 7.34 (t, J=7.7 Hz, 1H), 7.29-7.19 (m, 2H), 6.94 (d, J=8.5 Hz, 1H), 6.71 (dq, J=13.8, 6.9 Hz, 1H), 6.61 (s, 1H), 5.46 (d, J=13.6 Hz, 1H), 1.71 (d, J=6.9 Hz, 3H).

Catalyst 6 was synthesized from S2+S8 using the same procedure as that described for catalyst 4 from S2+S4, obtained as a pale yellow solid in 55% yield; $[α]_D^{24}$=88.0° (c=0.167 g/100 mL, CH$_2$Cl$_2$); $^1$H NMR (400 MHz, CDCl$_3$, TMS): δ 9.72 (brs, 1H), 8.93 (d, J=4.4 Hz, 1H), 8.64 (brs, 1H), 8.22-8.20 (m, 1H), 8.05 (d, J=8.8 Hz, 1H), 7.95 (d, J=8.0 Hz, 1H), 7.76 (d, J=4.0 Hz, 1H), 7.65-7.43 (m, 7H), 7.26-7.21 (m, 2H), 7.07-7.01 (m, 2H), 6.78 (d, J=8.4 Hz, 1H), 6.71-6.59 (m, 2H), 5.86 (s, 1H), 5.65 (dd, J=15.2 and 1.6 Hz, 1H), 3.68-3.65 (m, 1H), 3.10 (brs, 1H), 2.91-2.85 (m, 1H), 2.71-2.61 (m, 2H), 2.11-2.07 (m, 1H), 1.72-1.60 (m, 7H), 1.46-1.40 (m, 1H), 1.10-1.02 (m, 4H); $^{13}$C NMR (100 MHz, CDCl$_3$): δ 179.4, 172.9, 164.1, 150.4, 145.9, 144.6, 140.9, 136.4, 135.5, 134.6, 132.2, 131.8, 131.7, 131.6, 130.5, 128.9, 128.5, 128.3, 127.9, 127.0, 126.7, 125.9, 125.8, 125.5, 125.4, 125.3, 125.0, 124.2, 123.8, 122.6, 121.0, 119.7, 117.9, 77.0 (2), 72.4, 56.4, 54.2, 46.7, 32.8, 27.3, 23.6, 23.3, 17.6, 7.3; IR ν/cm$^{-1}$ 3241 (brs), 2933 (m), 2880 (m), 1671 (m), 1594 (m), 1500 (m), 1273 (m), 817 (m), 726 (m); HRMS (positive ESI) calcd for C$_{44}$H$_{42}$N$_5$O$_2$S$^{+1}$ ([M+H]$^+$): 704.3054; Found: 704.3074.

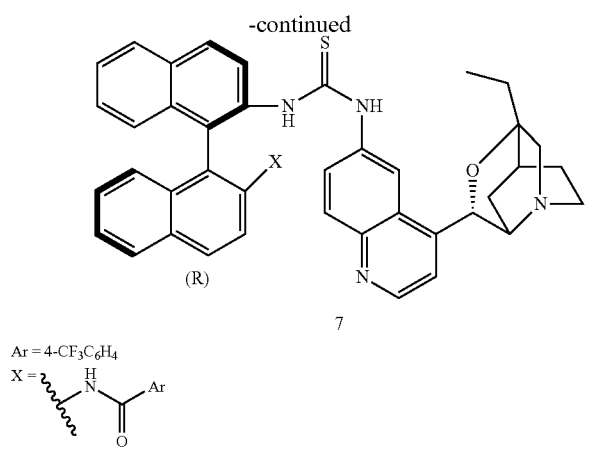

Ar = 4-CF₃C₆H₄

X =

7

To a solution of (R)-(+)-1,1'-binaphthyl-2,2'-diamine (0.284 g, 1.0 mmol) in 10 mL of dried CH₂Cl₂ was added solution of (4-CF₃C₆H₄CO)₂O (362.2 mg, 1.0 mmol) in CH₂Cl₂ (5 mL), at 0° C. under N₂. The resulting solution was stirred for overnight at room temperature, and 2N NaOH aqueous solution was added to adjust the solution to pH≈7. The reaction mixture was extracted with CH₂Cl₂ and the combined organic phases were washed with saturated brine and dried over anhydrous Na₂SO₄. The solution was filtered and concentrated under reduced pressure. The residue was purified by column chromatography on silica gel (hexane/EtOAc=5/1) to give product S9 (42% yield) as a pale yellow solid. ¹H NMR (400 MHz, CDCl₃, TMS): δ 8.85 (d, J=9.0 Hz, 1H), 8.06 (d, J=9.1 Hz, 1H), 7.94 (d, J=8.2 Hz, 1H), 7.91 (s, 1H), 7.88 (d, J=8.8 Hz, 1H), 7.85-7.82 (m, 1H), 7.52-7.42 (m, 1H), 7.38-7.18 (m, 8H), 7.16 (d, J=8.8 Hz, 1H), 6.98 (d, J=8.4 Hz, 1H), 3.71 (s, 2H).

S9 (130 mg, 0.28 mmol) was dissolved in CH₂Cl₂ (5 mL) and sat. aq. NaHCO₃ (5 mL) was added. The resulting biphasic solution was cooled to 0° C. and thiophosgene (0.03 mL, 0.34 mmol, 1.3 equiv) was then carefully added. The reaction was allowed to warm to room temperature and stirred for 12 h. The layers were separated and the aqueous layer was extracted with CH₂Cl₂. The organic layers were collected, washed with brine, dried over anhydrous sodium sulfate. The solution was filtered and concentrated under reduced pressure. The residue was purified by column chromatography on silica gel (hexane/EtOAc=10/1) to give product S10 (80% yield) as a pale yellow solid. ¹H NMR (400 MHz, CDCl₃, TMS): δ 8.77 (d, J=8.4 Hz, 1H), 8.26-7.93 (m, 4H), 7.68-6.98 (m, 12H).

Catalyst 7 was synthesized from S2+S10 using the same procedure as that described for catalyst 4 from S2+S4, obtained as a pale yellow solid in 82% yield; [α]$_D^{24}$=133.0° (c=0.167 g/100 mL, CH₂Cl₂); ¹H NMR (400 MHz, CDCl₃, TMS): δ 9.53 (brs, 1H), 8.88 (d, J=4.0 Hz, 1H), 8.45-8.34 (m, 2H), 8.20 (d, J=9.6 Hz, 1H), 7.94 (d, J=9.2 Hz, 1H), 7.86 (d, J=8.8 Hz, 1H), 7.71-7.50 (m, 4H), 7.45-7.33 (m, 6H), 7.19-7.08 (m, 4H), 7.01-6.97 (m, 1H), 6.84-6.82 (m, 1H), 6.46 (brs, 1H), 5.74 (s, 1H), 3.52-3.49 (m, 1H), 3.03-3.02 (m, 1H), 2.77-2.72 (m, 1H), 2.59-2.42 (m, 2H), 2.02-1.98 (m, 1H), 1.62-1.49 (m, 4H), 1.36-1.34 (m, 1H), 0.99-0.94 (m, 4H); ¹³C NMR (100 MHz, CDCl₃): δ 179.8, 172.9, 164.3, 150.5, 146.0, 144.5, 137.4, 136.5, 134.8, 134.3, 132.8 (q, J$_{C-F}$=32.5 Hz), 132.1, 131.9, 131.7, 131.0, 129.0, 128.8, 128.4, 128.0, 127.6, 127.3, 127.0, 126.2, 125.9, 125.5, 125.4, 125.2 (0), 125.1 (7), 125.1 (3), 124.8, 124.2, 123.1, 122.1, 119.7, 117.9, 77.0 (3), 72.5, 56.4, 54.3, 46.4, 32.8, 27.2, 23.6, 23.2, 7.2; IR ν/cm⁻¹ 3237 (m), 2934 (m), 2880 (m), 1668 (m), 1594 (m), 1499 (m), 1274 (m), 817 (m), 727 (m); HRMS (positive ESI) calcd for C₄₈H₄₁F₃N₅O₂S⁺¹ ([M+H]⁺): 808.2928; Found: 808.2928.

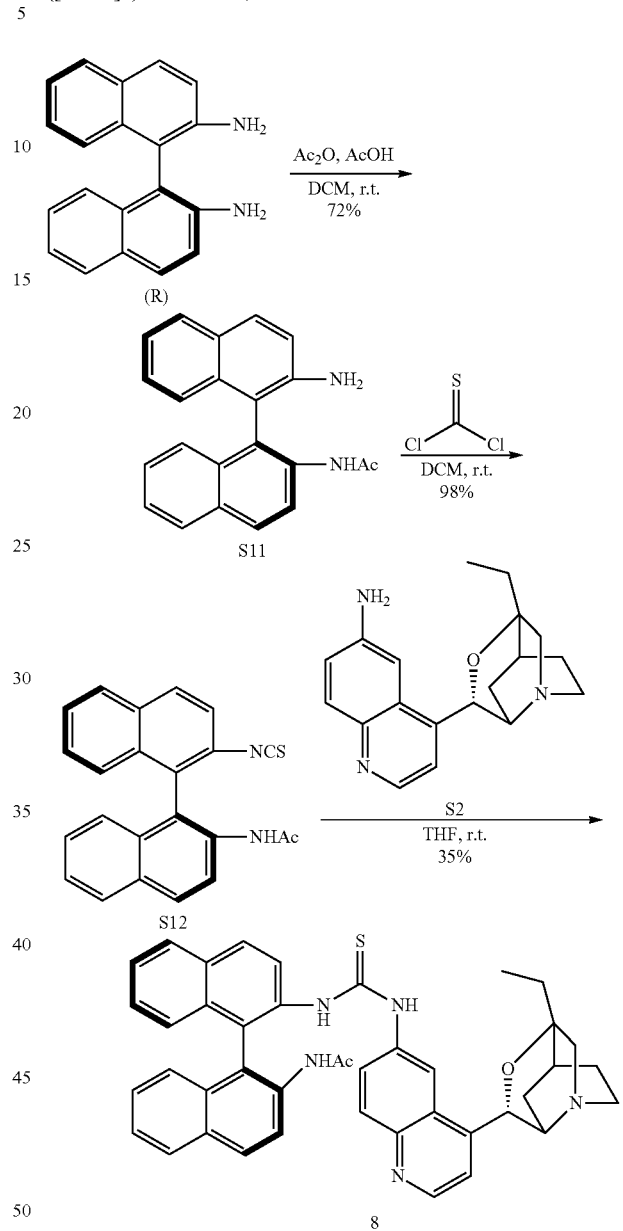

8

To a solution of (S)-(−)-1,1'-binaphthyl-2,2'-diamine (0.569 g, 2.0 mmol) and AcOH (1.5 mL) in 15 mL of dried CH₂Cl₂ was added acetic anhydride (1 mL, 10 mmol) at 0° C. under N₂. The resulting solution was stirred for overnight at room temperature, and 2N NaOH aqueous solution was added to adjust the solution to pH≈7. The reaction mixture was extracted with CH₂Cl₂ and the combined organic phases were washed with saturated brine and dried over anhydrous Na₂SO₄. The solution was filtered and concentrated under reduced pressure. The residue was purified by column chromatography on silica gel (hexane/EtOAc=2/1) to give product S11 (72% yield) as a white solid. ¹H NMR (400 MHz, CDCl₃, TMS): δ 8.60 (d, J=9.0 Hz, 1H), 7.98 (d, J=9.1 Hz, 1H), 7.89 (d, J=8.2 Hz, 1H), 7.83 (d, J=8.8 Hz, 1H), 7.80

(d, J=7.6 Hz, 1H), 7.42-7.36 (m, 1H), 7.27-7.15 (m, 5H), 7.01 (s, 1H), 6.89 (d, J=8.3 Hz, 1H), 3.65 (s, 2H), 1.83 (s, 3H).

S11 (360 mg, 1.0 mmol) was dissolved in $CH_2Cl_2$ (10 mL) and sat. aq. $NaHCO_3$ (10 mL) was added. The resulting biphasic solution was cooled to 0° C. and thiophosgene (0.11 mL, 1.43 mmol, 1.3 equiv.) was then carefully added. The reaction was allowed to warm to room temperature and stirred for 12 h. The layers were separated and the aqueous layer was extracted with $CH_2Cl_2$. The organic layers were collected, washed with brine, dried over anhydrous sodium sulfate. The solution was filtered and concentrated under reduced pressure to get pure product 512 (98% yield) as a pale yellow solid, which was used directly in the subsequent reaction without further purification. $^1H$ NMR (400 MHz, $CDCl_3$, TMS): δ 8.53 (d, J=7.8 Hz, 1H), 8.01 (dd, J=13.4, 8.9 Hz, 2H), 7.97-7.89 (m, 2H), 7.55-7.49 (m, 1H), 7.47 (d, J=8.8 Hz, 1H), 7.42 (t, J=7.4 Hz, 1H), 7.38-7.32 (m, 1H), 7.29-7.19 (m, 2H), 6.95 (d, J=8.4 Hz, 1H), 6.62 (s, 1H), 1.80 (s, 3H).

Catalyst 8 was synthesized from S2+S12 using the same procedure as that described for catalyst 4 from S2+S4, obtained as a pale yellow solid in 35% yield; $[\alpha]_D^{23}$=26.4° (c=0.167 g/100 mL, $CH_2Cl_2$); $^1H$ NMR (400 MHz, $CDCl_3$, TMS): δ 9.36 (brs, 1H), 8.82 (d, J=4.4 Hz, 1H), 8.32 (brs, 1H), 8.19 (d, J=9.2 Hz, 1H), 8.00 (d, J=8.8 Hz, 1H), 7.90 (d, J=8.8 Hz, 1H), 7.68-7.58 (m, 4H), 7.46-7.40 (m, 3H), 7.49-7.17 (m, 3H), 7.03-7.00 (m, 2H), 6.77 (d, J=8.4 Hz, 1H), 6.51 (brs, 1H), 5.63 (s, 1H), 3.42 (d, J=13.6 Hz, 1H), 3.23-3.21 (m, 1H), 2.84-2.82 (m, 2H), 2.51 (d, J=13.6 Hz, 1H), 2.08-2.05 (m, 1H), 1.76 (s, 3H), 1.62-1.52 (m, 4H), 1.45-1.39 (m, 1H), 1.19-1.13 (m, 1H), 0.92 (t, J=7.2 Hz, 3H); $^{13}C$ NMR (100 MHz, $CDCl_3$): δ 181.0, 169.2, 160.4, 150.1, 145.8, 144.2, 136.2, 135.1, 135.0, 132.4, 132.3, 132.2, 131.3, 130.7, 128.8, 128.7, 128.1, 128.0, 126.9, 126.8, 126.2, 126.1, 126.0, 125.4 (4), 125.4 (1), 125.2, 124.6, 122.2, 121.7, 119.4, 118.1, 77.1, 72.6, 56.3, 54.3, 46.4, 32.8, 27.1, 24.2, 23.8, 23.3, 7.2; IR v/$cm^{-1}$ 3234 (brs), 2962 (m), 2880 (m), 1668 (m), 1595 (m), 1500 (s), 1274 (m), 908 (m), 817 (m), 726 (m); HRMS (positive ESI) calcd for $C_{42}H_{40}N_5O_2S^{+1}$ ([M+H]$^+$): 678.2897; Found: 678.2907.

Caution:

Catalysts 4-8 can undergo slow methanolysis, especially at the end of the evaporation, and must be concentrated at 0° C. The purities were slightly improved when the evaporation was stopped when the products started to become viscous, then a small amount of $CH_2Cl_2$ was added and the product was finally concentrated under vacuum by an oil pump. The pure products are sensitive to moisture and carbon dioxide and should be stored in a glovebox.

Example 2. Polymer Characterizations

Polymer number-average molecular weight ($M_n$) and molecular weight distributions or polydispersity indices (Đ=$M_w/M_n$) were measured by gel permeation chromatography (GPC) analyses carried out at 40° C. and a flow rate of 1.0 mL/min, with DMF as the eluent on a Waters University 1500 GPC instrument equipped with one PLgel 5 μm guard and three PLgel 5 μm mixed-C columns (Polymer Laboratories; linear range of MW=200-2,000,000). The instrument was calibrated with 10 PMMA standards, and chromatograms were processed with Waters Empower software (version 2002). Glass transition temperatures ($T_g$) and melting temperatures ($T_m$) of the polymers were measured by differential scanning calorimetry (DSC) on a Q20 DSC, TA Instruments. Polymer samples were first heated to 200 at 10° C./min, equilibrated at this temperature for 3 min, then cooled to −50° C. at 10° C./min, held at this temperature for 3 min, and reheated to 250° C. at 10° C./min. All thermal data were obtained from the second scan. Tacticity of polymers was determined from the methine region of the homo-decoupled $^1H$ NMR spectrum. $P_m$, the probability of forming a new isotactic dyad, was calculated utilizing methods established in the literature (Kasperczyk, *Macromolecules* 1995, 28, 3937-3939; Coudane et al., *J. Polym. Sci., Part A: Polym. Chem.* 1997, 35, 1651-1658).

Example 3. General Procedure for Epimerization of meso-LA

Epimerization of meso-LA was performed in a glovebox. To a solution of meso-LA (2.88 g, 20 mmol) in anhydrous toluene (8 mL) was added $B(C_6F_5)_3$ (1 mL, 0.002 M in toluene) and DABCO (1 mL, 0.002 M in toluene). The mixture was stirred at room temperature for 22 h, then "wet" dichloromethane (10 mL) mixed with 250 ppm of benzoic acid was added to quench the reaction and obtain a homogeneous solution and 0.2 mL aliquots were withdrawn from the solution and analyzed by $^1H$ NMR for determination of meso-LA conversion. See Table A for tabulated results.

Example 4. Procedure I for Isolation of the Pure Rac-LA

Figure 4:
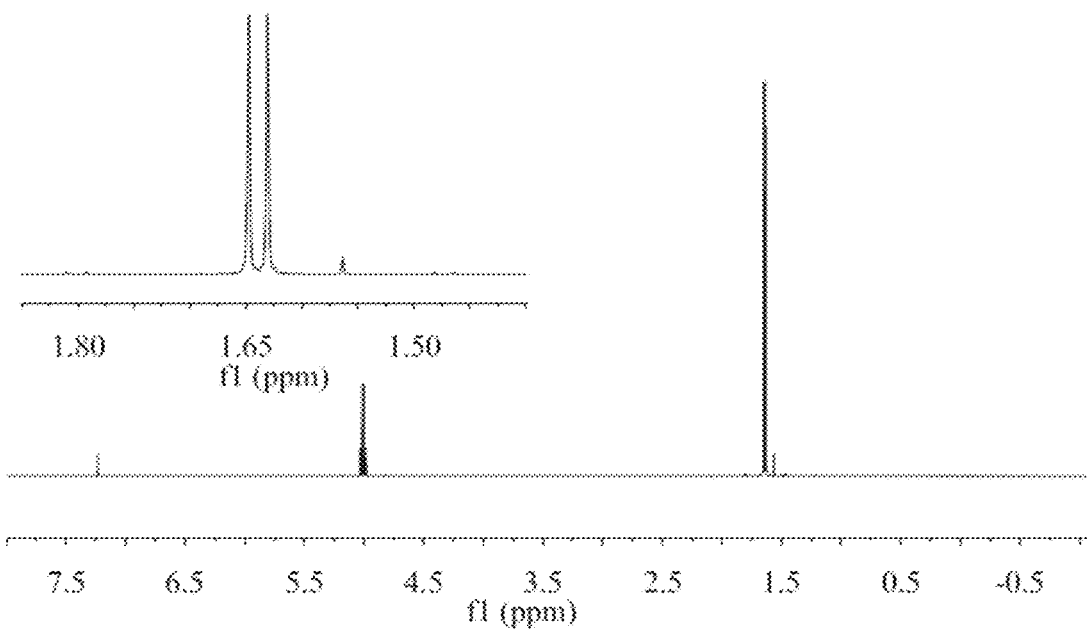
FIG. 4. NMR (CDCl$_3$, 25° C.) spectrum of pure rac-LA (run 38, Table A). The two small peaks at δ 7.26 and 1.56 ppm are residual NMR solvent peaks due to CHCl$_3$ and water.

Epimerization of meso-LA was performed in a glovebox. To a solution of meso-LA (5.76 g, 40 mmol) in anhydrous toluene (19.2 mL) was added $B(C_6F_5)_3$ (0.4 mL, 0.002 M in toluene) and DABCO (0.4 mL, 0.002 M in toluene). The mixture was stirred at room temperature for 10 h, after which time the resulting suspension was filtered and washed with cold toluene (15 mL) twice, and dried under vacuum at room temperature to give the pure rac-LA (run 38, Table A and FIG. 4) as a white solid (5.08 g, yield: 88.2%). The filtrate was a mixture of rac-LA and meso-LA in a 95:5 ratio.

Example 5. Procedure II for Isolation of Rac-LA with >98% Purity

Figure 5:
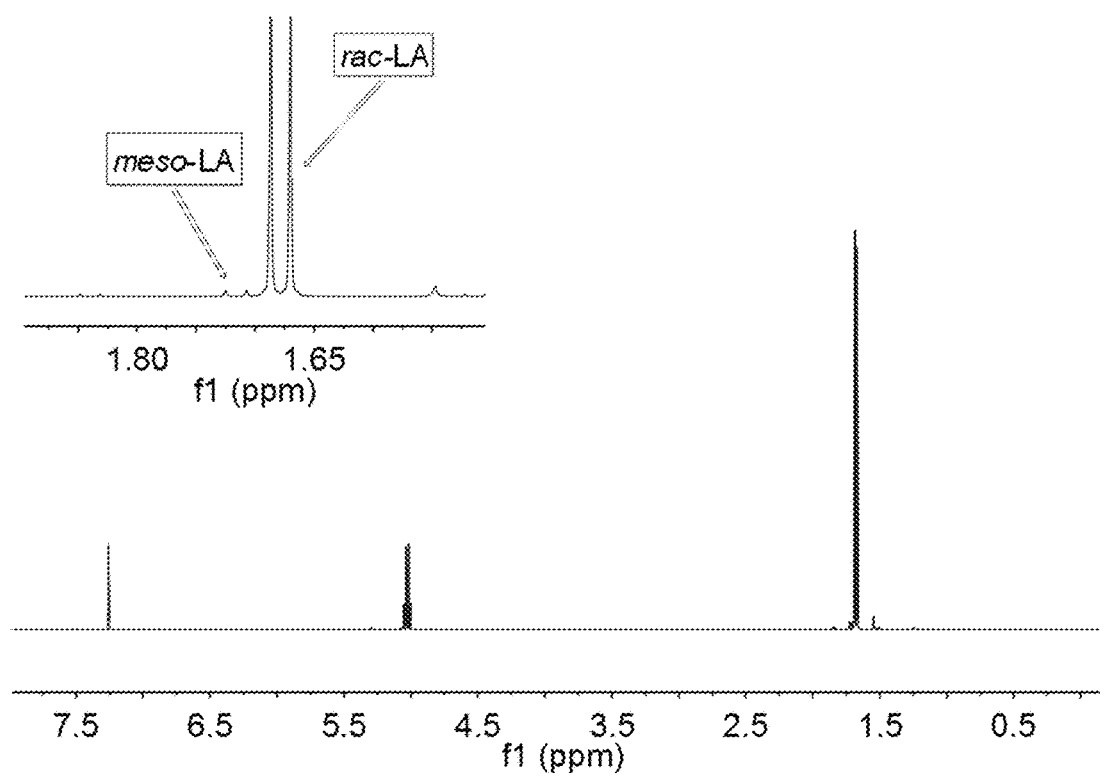
FIG. 5. $^1$H NMR (CDCl$_3$, 25° C.) spectrum of rac-LA (run 37, Table A). The two small peaks at δ7.26 and 1.56 ppm are residual NMR solvent peaks due to CHCl$_3$ and water.

To a solution of meso-LA (2.88 g, 20 mmol) in anhydrous toluene (8 mL) was added $B(C_6F_5)_3$ (0.2 mL, 0.002 M in toluene) and DABCO (0.2 mL, 0.002 M in toluene). The mixture was stirred at room temperature for 22 h, after which the reaction mixture was concentrated and the crude product was purified by flash chromatograph on silica gel (Hexane/EtOAc=1/1) to give the product (2.84 g, 98.6% yield, run 37, Table A) in a rac-LA/meso-LA ration of 55.4/1 (FIG. 5).

Example 6. General Procedures for Kinetic Resolution of Rac-LA

Polymerizations were performed in 25 mL glass reactors inside the glovebox for ambient temperature (~25° C.) runs, or in 25 mL Schlenk flasks interfaced to a dual-manifold Schlenk line with an external temperature bath for runs at other temperatures. In a typical polymerization reaction, catalyst (0.05 mmol) and BnOH (5.4 mg, 0.05 mmol) were dissolved in 3 mL of dichloromethane. Immediately thereafter, rac-LA (720.6 mmg, 5 mmol) was added as a solid to the vigorously stirred solution. At predetermined time intervals 0.2 mL aliquots were withdrawn from the polymerization reaction using a syringe and quickly quenched into 1 mL septum cap sealed vials containing 0.6 mL of undried "wet" $CDCl_3$ mixed with 250 ppm of BHT. The quenched aliquots were analyzed by $^1H$ NMR for monomer conversion. The solvent was removed via roto-vap, and the unreacted monomer was extracted with a 1:1 hexane:$^i$PrOH solution, filtered through a 0.2 μm syringe filter, and the % ee of the monomer was measured using an Agilent 1100

Series HPLC with a flow rate of 0.5 mL/min, utilizing a Chiracel IA column at 30° C. (90:10 hexane:$^i$PrOH; 0.5 mL/min; L-LA: 22.6 min; D-LA: 25.2 min). The selectivity factor, s, was determined from the equation s={ln [(1−c)(1−ee)]}/{ln [(1−c)(1+ee)]}, where c is the monomer conversion and ee is the enantiomeric excess of the unreacted monomer. Polymerizations were quenched at the time specified in Table 2 with 5 mL of methanol, and the polymer was precipitated into 50 mL of methanol and collected by filtration before being washed extensively with methanol to remove any catalyst residue or unreacted monomer and dried in a vacuum oven at room temperature to a constant weight.

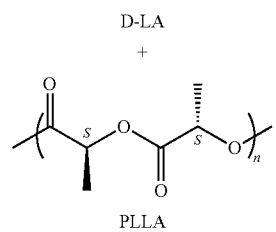

D-LA
+
PLLA

TABLE 2

Results of Kinetic Resolution of Rac-LA by β-ICD.

| Run | I | Monomer/ICD/I | Solvent[a] | Time (h) | Conv[b] (%) | ee[c] (%) | $k_S/k_R$[d] (s) | $M_n$[e] (kg/mol) | Đ[e] ($M_w/M_n$) |
|---|---|---|---|---|---|---|---|---|---|
| 1 | BnOH | 100/1/1 | DCM (5M)[f] | 14 | 60.2 | 21.6 | 1.6 | 13.8 | 1.12 |
| 2 | BnOH | 100/1/1 | DCM (2.5M)[f] | 14 | 50.2 | 34.9 | 1.7 | 10.8 | 1.11 |
| 3 | BnOH | 100/1/1 | DCM (1.67M) | 25 | 47.4 | 39.5 | 3.7 | 11.5 | 1.10 |
| 4 | BnOH | 100/1/1 | DCM (1.25M) | 36 | 45.0 | 32.5 | 3.1 | 10.7 | 1.10 |
| 5 | BnOH | 100/1/1 | DCM (1M) | 49 | 45.4 | 31.2 | 2.9 | 10.7 | 1.10 |
| 6 | BnOH | 100/1/1 | TOL (1.67M)[f] | 120 | 30.7 | 7.3 | 1.5 | 6.16 | 1.12 |
| 7 | BnOH | 50/1/1 | DCM (1.67M) | 6 | 47.6 | 40.2 | 3.8 | 5.53 | 1.14 |
| 8 | BnOH | 100/2/1 | DCM (1.67M) | 12 | 48.3 | 29.1 | 2.5 | 10.8 | 1.10 |
| 9 | BnOH | 100/1/2 | DCM (1.67M) | 11 | 49.5 | 40.2 | 3.5 | 7.09 | 1.08 |
| 10 | BnOH | 100/1/5 | DCM (1.67M) | 4.5 | 56.8 | 50.1 | 3.5 | 3.42 | 1.10 |
| 11 | DPM[g] | 100/1/1 | DCM (1.67M) | 24 | 47.4 | 29.7 | 1.3 | 11.0 | 1.11 |
| 12 | DPE[h] | 100/1/1 | DCM (1.67M) | 24 | 50.0 | 33.7 | 2.7 | 11.5 | 1.10 |
| 13 | PB[i] | 100/1/1 | DCM (1.67M) | 24 | 49.0 | 40.4 | 3.6 | 10.9 | 1.10 |

[a] Concentration of rac-LA is given in parentheses.
[b] Determined by $^1$H NMR in CDCl$_3$. [c] Enantiomeric excess of unreacted monomer measured by chiral HPLC.
[d] Calculated from s = {ln[(1 − c)(1 − ee)]}/{ln[(1 − c)(1 + ee)]}.
[e] Number-average molecular weight ($M_n$) and molecular weight distribution (Đ = $M_w/M_n$) were determined by GPC at 40° C. in DMF relative to PMMA standards.
[f] Partially insoluble in solvent.
[g] Diphenylmethanol.
[h] 2,2-diphenylethan-1-ol.
[i] 4-(pyren-1-yl)butan-1-ol.

Example 7. General Procedure for One-Pot Process

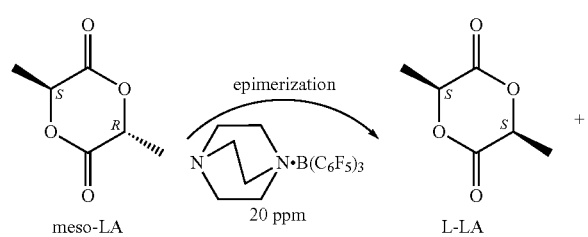

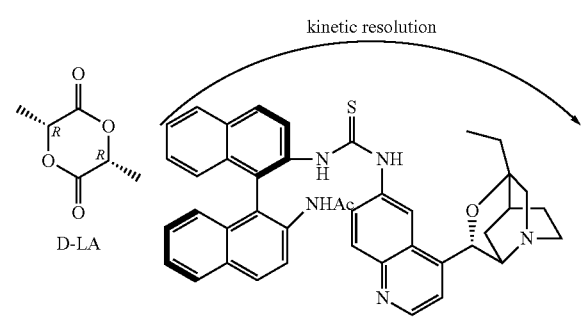

All operations were performed in a glovebox. To a solution of meso-LA (2.88 g, 20 mmol) in anhydrous toluene (8 mL) was added B(C$_6$F$_5$)$_3$ (1 mL, 0.002 M in toluene) and DABCO (1 mL, 0.002 M in toluene). The mixture was stirred at room temperature for 22 h, and was dried under vacuum to obtain a white solid with a rac-LA/meso-LA ratio of 99/1, which was used directly in the subsequent kinetic resolution polymerization by catalyst 4. The procedure for the kinetic resolution polymerization was the same as described above, and the results are listed in Table 1, run 11.

Example 8. Practical Conditions for Bulk Conversion of Meso-LA to Rac-LA

Meso-lactide is often an 'impurity' in the preparation of lactide from lactic acid. The methods described herein can be used to epimerize meso-lactide to racemic lactide even if the meso-lactide contains significant amounts of racemic lactide and/or other impurities such as oligomers, lactic acid, and/or various protic impurities (which composition can be referred to as 'plant grade' lactide). The following example provide ways to simplify the epimerization methods described herein by providing methods of pretreating plant grade lactide prior to epimerization with a Lewis base pair, therefore significantly lowering the amount of expensive Lewis acid required for the epimerization.

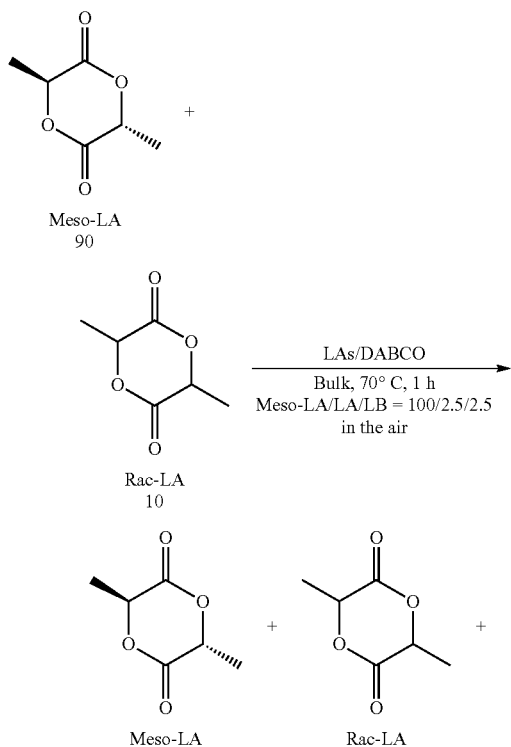

Meso-LA
90

Rac-LA
10

LAs/DABCO
Bulk, 70° C, 1 h
Meso-LA/LA/LB = 100/2.5/2.5
in the air

Meso-LA + Rac-LA + Oligomer

Reaction run in air.

To a 25 mL vial in glovebox, was added $B(C_6F_5)_3$ (128 mg, 0.25 mmol), meso-LA (1.44 g, 10 mmol) and DABCO (28 mg, 0.25 mmol). The vial was open to air and placed in a temperature-controlled orbit shaker (70° C. or 85° C., 300 rpm) and heated for 1 h, then "wet" dichloromethane (10 mL) mixed with 250 ppm of benzoic acid was added to quench the reaction and obtain a homogeneous solution and 0.2 mL aliquots were withdrawn from the solution and analyzed by $^1$H NMR for determination of meso-LA conversion. (meso-LA, $B(C_6F_5)_3$ and DABCO were not purified.)

| Run [a] | Lewis acid (LAs) | Meso/Rac/Oligomer [b] |
|---|---|---|
| 1 | $B(C_6F_5)_3$ | 13/60/27 |
| 2 [c] | $B(C_6F_5)_3$ | 1/99/0 |
| 3 [d] | $B(C_6F_5)_3$ | 82/18/0 |
| 4 [e] | $B(C_6F_5)_3$ | 90/10/0 |
| 5 | $B(C_6F_5)_3$ | 25/47/28 |
| 6 | $BF_3 \cdot Et_2O$ | 90/10/0 |
| 7 | $Al[O(CCH_3)_3]_3$ | 18/62/20 |
| 8 | $AlCl_3$ | 75/25/0 |
| 9 | $ZnCl_2$ | 19/31/50 |
| 10 | $MgBr_2$ | 8/27/65 |

[a] Rac-LA/meso-LA = 1/9 (plant-grade) as starting material.
[b] Determined by $^1$H NMR in $CDCl_3$.
[c] At 85° C., 2.5% $B(C_6F_5)_3$.
[d] At 85° C., 1.0% $B(C_6F_5)_3$.
[e] At 85° C., 0.5% $B(C_6F_5)_3$.

Results for Pretreatment of Crude Meso-LA with an Inexpensive Lewis Acid.

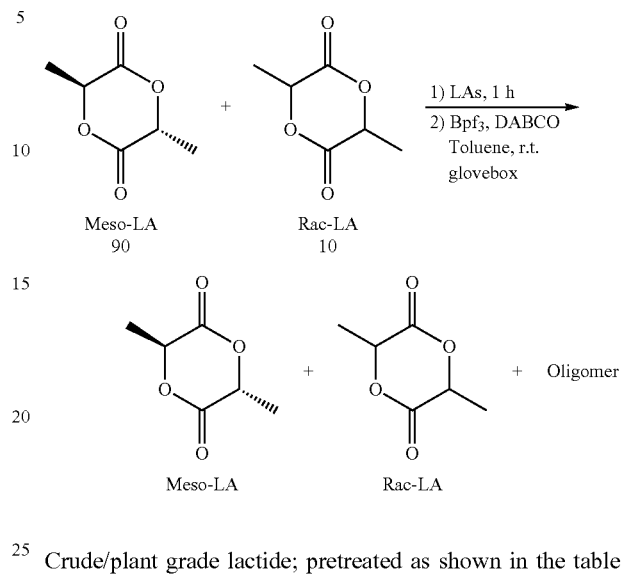

Crude/plant grade lactide; pretreated as shown in the table below; lower loading of Lewis acid required as a result of pretreatment (e.g., lowered Lewis acid requirement by 25-fold for complete near quantitative epimerization).

| Run [a] | LAs (%) [b] | $B(C_6F_5)_3$ (%) [b] | DABCO (%) [b] | t (h) | Meso/Rac/Oligomer [c] |
|---|---|---|---|---|---|
| 1 | $BF_3 \cdot Et_2O$ (5) | 0.1 | 5 | 4 | 90/10/0 |
| 2 | $ZnCl_2$ (5) | 0.1 | 5 | 4 | 90/10/0 |
| 3 | $MgBr_2$ (5) | 0.1 | 5 | 4 | 74/13/13 |
| 4 | $AlCl_3$ (5) | 0.1 | 5 | 4 | 2/98/0 |
| 5 | $AlCl_3$ (5) | 0.01 | 5 | 9 | 63/37/0 |
| 6 | $AlCl_3$ (2) | 0.1 | 5 | 4 | 50/50/0 |
| 7 | $AlCl_3$ (1) | 0.1 | 5 | 9 | 90/10/0 |
| 8 | $AlCl_3$ (5) | 0.1 | 0.1 | 4 | 90/10/0 |
| 9 [d] | $AlCl_3$ (5) | 0.1 | 5 | 12 | 64/36/0 |

[a] Rac-LA/meso-LA = 1/9 (plant-grade) as starting material.
[b] Used directly as received.
[c] Determined by $^1$H NMR in $CDCl_3$.
[d] Toluene was undried in the air.

General Procedure for Epimerization of meso-LA Treated with an Inexpensive Lewis Acid First.

Epimerization of meso-LA was performed in a glovebox. To a solution of meso-LA (722 mg, 5 mmol) in anhydrous toluene (2.5 mL) was added $AlCl_3$ (33.3 mg, 0.25 mmol). The mixture was stirred at room temperature for 1 h, then was added $B(C_6F_5)_3$ (2.56 mg, 0.005 mmol), DABCO (28 mg, 0.25 mmol) and stirred at room temperature for another 4 h, then "wet" dichloromethane (10 mL) mixed with 250 ppm of benzoic acid was added to quench the reaction and obtain a homogeneous solution and 0.2 mL aliquots were withdrawn from the solution and analyzed by $^1$H NMR for determination of meso-LA conversion.

Meso-lactide for the following experiments was pretreated with $AlCl_3$ (5 mol % with respect to lactide) at 70° C., and further purified by sublimation under vacuum to remove residual $AlCl_3$ and byproducts.

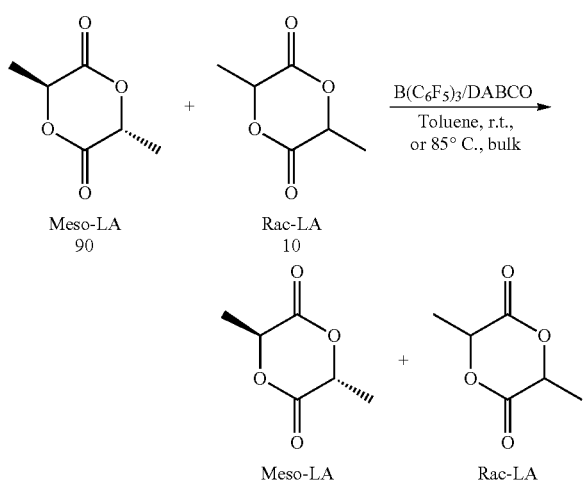

| Run[a] | B(C$_6$F$_5$)$_3$ (%)[b] | DABCO (%)[b] | t (h) | Meso/Rac/Oligomer[c] |
|---|---|---|---|---|
| 1 | 0.1 | 0.1 | 1 | 2/98/0 |
| 2 | 0.01 | 0.01 | 1 | 2/98/0 |
| 3[d] | 0.1 | 0.1 | 1 | 90/10/0 |
| 4[e] | 0.1 | 0.1 | 1 | 2/98/0 |
| 5[f] | 0.1 | 0.1 | 1 | 15/85/0 |

[a] Rac-LA/meso-LA = 1/9 as starting material.
[b] Used directly as received.
[c] Determined by $^1$H NMR in CDCl$_3$.
[d] Toluene was undried; reaction run in air.
[e] Toluene was dried; reaction run in air.
[f] Borane-DABCO adduct (0.1%) at 85° C. in bulk.

This example therefore provides a useful method to pretreat crude or plant grade lactide such that the epimerization described herein can be carried out with significantly lower levels of (potentially expensive) Lewis acids and/or bases. The plant grade lactide can be sublimed prior to and/or after pretreatment, and/or the pretreated plant grade lactide can be pretreated and then the epimerization can be carried out directly. In one specific embodiment, plant grade lactide containing both racemic lactide and meso-lactide is pretreated with 5 mol % AlCl$_3$, sublimed, and then epimerized with a Lewis base pair, for example, using one or more of the conditions in the table immediately above.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method to epimerize meso-lactide into racemic lactide comprising contacting meso-lactide and a Lewis acid/base pair for a period of time sufficient to epimerize meso-lactide to racemic lactide, wherein at least about 0.001 mol % of the Lewis acid/base pair is present with respect to the initial molar amount of meso-lactide.

2. The method of claim 1 wherein the Lewis acid/base pair is a boron/nitrogen Lewis acid/base pair.

3. The method of claim 1 wherein the Lewis acid of the Lewis acid/base pair is B(C$_6$F$_5$)$_3$.

4. The method of claim 1 wherein the Lewis base of the Lewis acid/base pair is 1,4-diazabicyclo [2.2.2]octane (DABCO) or triethylamine.

5. The method of claim 1 wherein at least about 80% of the meso-lactide is epimerized into racemic lactide.

6. The method of claim 1 wherein the contacting is carried out in the presence of solvent, wherein meso-lactide is soluble in the solvent at 25° C. and racemic lactide is not soluble in the solvent at 25° C.

7. The method of claim 6 wherein the initial concentration of the meso-lactide in the solvent is at least about 0.2 M.

8. The method of claim 6 wherein the initial concentration of the meso-lactide in the solvent is about 1 M to about 3 M.

9. The method of claim 6 wherein the method is carried out at about 0° C. to about 100° C.

10. The method of claim 1 wherein the contacting is carried out in the absence of solvent.

11. The method of claim 10 wherein the meso-lactide is heated to at least about 54° C. but not more than about 116° C.

12. The method of claim 1 wherein the concentration of the Lewis acid/base pair is about 10 ppm to about 5 mol % with respect to the meso-lactide.

13. The method of claim 1 further comprising isolating substantially pure racemic lactide after meso-lactide has been epimerized into racemic lactide, wherein the isolating comprises one or more of filtering, washing, and chromatographing the racemic lactide.

14. The method of claim 1 further comprising kinetic resolution of the racemic lactide by contacting the racemic lactide with a compound of Formula I:

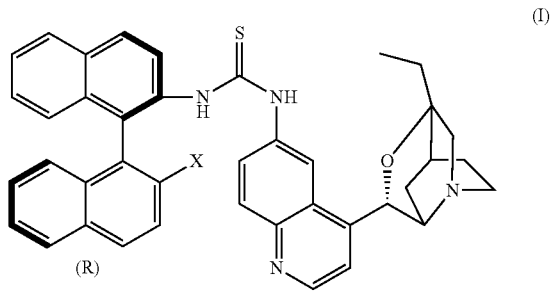

wherein X is —NH—C(═O)—R, wherein R is —CH$_3$, —CF$_3$, 2-propenyl, or optionally substituted aryl;
under suitable conditions to initiate ring-opening polymerization of L-lactide to provide a mixture of isotactic poly(L-lactide) and D-lactide.

15. The method of claim 14 wherein the compound of Formula I is compound 4:

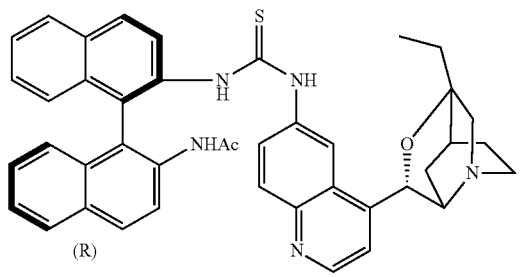

(4)

16. The method of claim 14 further comprising separating the isotactic poly(L-lactide) and D-lactide.

17. The method of claim 1 wherein the meso-lactide prior to epimerization is in a composition that comprises one or more impurities selected from racemic lactide, lactic acid, lactic acid salts, and oligomers of lactide.

18. The method of claim 17 wherein the composition that comprises one or more impurities is treated, prior to epimerization, by a method comprising contacting the composition with about 1 mol % to about 10 mol % of $AlCl_3$ prior to contacting the meso-lactide with the Lewis acid/base pair.

19. The method of claim 18 wherein the composition, after having been contacted with the $AlCl_3$, is purified prior to epimerization.

20. A compound of Formula I:

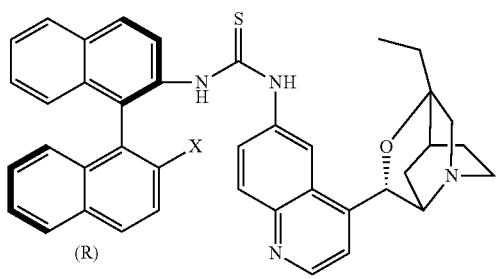

(I)

wherein X is —NH—C(=O)—R, wherein R is —$CH_3$, —$CF_3$, 2-propenyl, or optionally substituted aryl.

* * * * *